United States Patent
Deshayes et al.

(10) Patent No.: US 11,905,338 B2
(45) Date of Patent: Feb. 20, 2024

(54) PEPTIDES FOR USE AS CELL-PENETRATING PEPTIDES

(71) Applicants: CENTRE NATIONAL DE LA RECHERCHE SCIENTIFIQUE, Paris (FR); UNIVERSITE DE MONTPELLIER, Montpellier (FR)

(72) Inventors: Sébastien Deshayes, Montpellier (FR); Karidia Konate, Montpellier (FR); Eric Vives, Castelnau le Lez (FR); Gudrun Aldrian, Prades-le-Lez (FR); Prisca Boisguerin, Montpellier (FR)

(73) Assignees: CENTRE NATIONAL DE LA RECHERCHE SCIENTIFIQUE, Paris (FR); UNIVERSITÉ DE MONTPELLIER, Montpellier (FR)

( * ) Notice: Subject to any disclaimer, the term of this patent is extended or adjusted under 35 U.S.C. 154(b) by 608 days.

(21) Appl. No.: 17/260,244

(22) PCT Filed: Jul. 16, 2019

(86) PCT No.: PCT/EP2019/069149
§ 371 (c)(1),
(2) Date: Jan. 14, 2021

(87) PCT Pub. No.: WO2020/016242
PCT Pub. Date: Jan. 23, 2020

(65) Prior Publication Data
US 2021/0292364 A1 Sep. 23, 2021

(30) Foreign Application Priority Data
Jul. 17, 2018 (EP) ..................... 18183966

(51) Int. Cl.
*C07K 7/08* (2006.01)
*A61K 9/51* (2006.01)
*C12N 15/113* (2010.01)

(52) U.S. Cl.
CPC ............ *C07K 7/08* (2013.01); *A61K 9/5169* (2013.01); *C12N 15/1137* (2013.01); *C12N 2310/14* (2013.01); *C12N 2320/32* (2013.01)

(58) Field of Classification Search
None
See application file for complete search history.

(56) References Cited

FOREIGN PATENT DOCUMENTS

| WO | WO 2011/020188 | 2/2011 | |
| WO | WO-2011020188 A1 * | 2/2011 | ........... A61K 31/713 |
| WO | WO 2013/075244 | 5/2013 | |

OTHER PUBLICATIONS

Chen, P. et al. "Cell permeabilization; delivery mechanism; drug delivery; peptide library; transfection" EBI Accession No. AZF22135, Mar. 31, 2011, p. 1, XP-002785305.
Konate, K. et al. "Optimisation of vectorisation property: A comparative study for a secondary amphipathic peptide" *International Journal of Pharmaceutics*, 2016, pp. 71-84, vol. 509, No. 1.
Written Opinion in International Application No. PCT/EP2019/069149, dated Sep. 27, 2019, pp. 1-8.

* cited by examiner

*Primary Examiner* — Dominic Lazaro
(74) *Attorney, Agent, or Firm* — SALIWANCHIK, LLOYD & EISENSCHENK

(57) ABSTRACT

The present invention relates to new peptides comprising an amino acid sequence LL-[X]n-LL, wherein X is selected from R, L and W, and n=10 to 12, and wherein [X]n comprises 4 R, 4 L and between 2 and 4 W, that may be used as cell-penetrating peptides. The present invention also relates to nanoparticles comprising a peptide of the invention and a cargo molecule and uses thereof.

17 Claims, 18 Drawing Sheets
Specification includes a Sequence Listing.

A

B

C
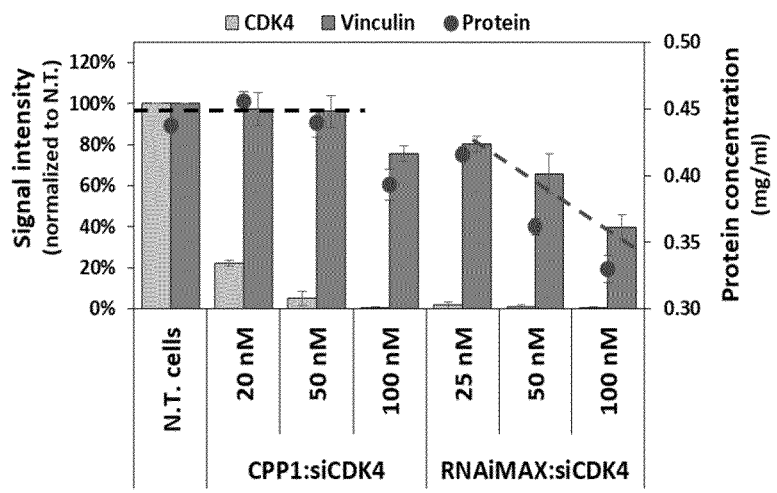
D
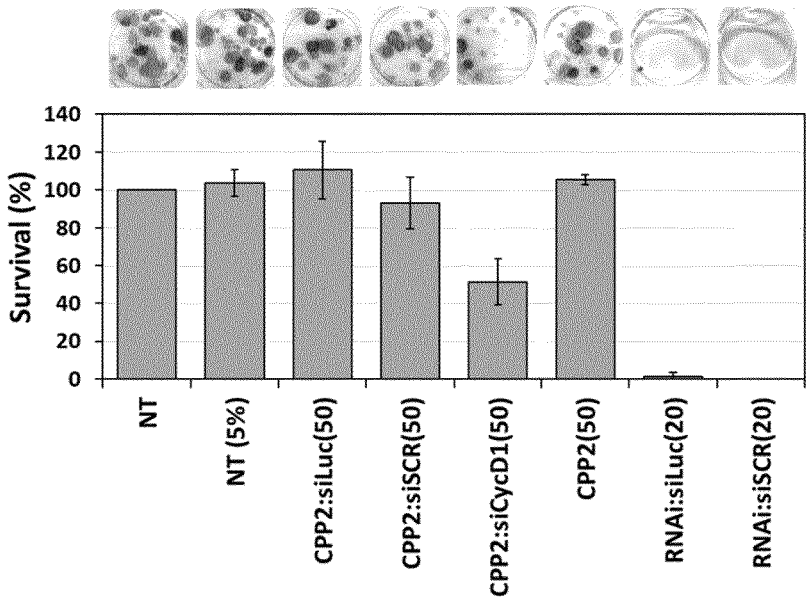
FIGURE 9 (Continue)

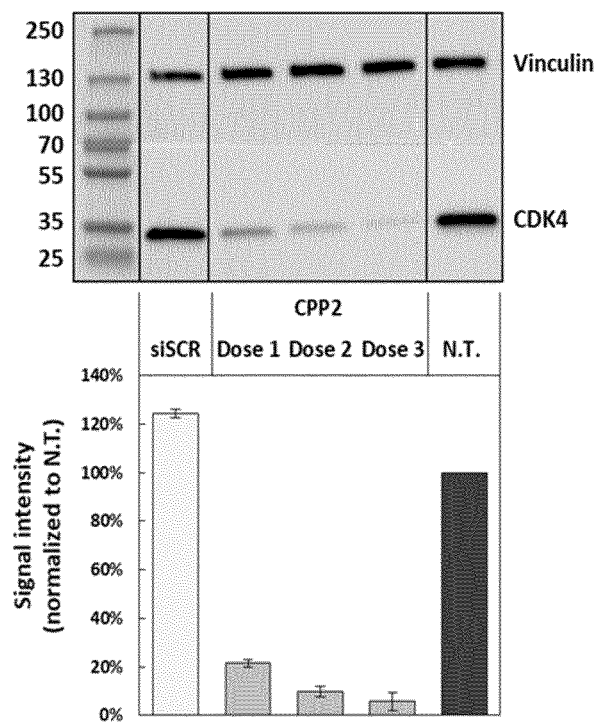
FIGURE 9 (Continue)

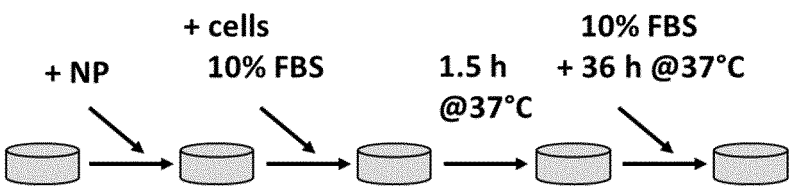
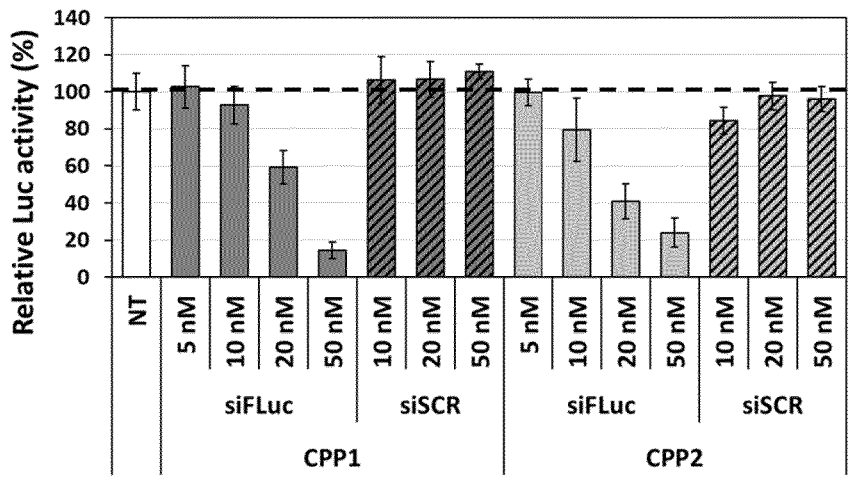
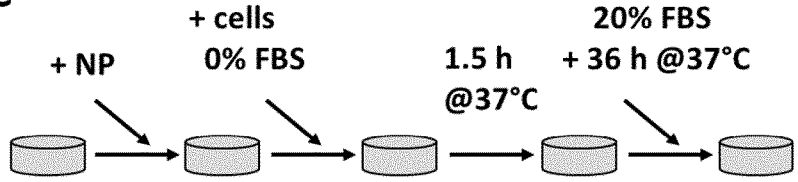
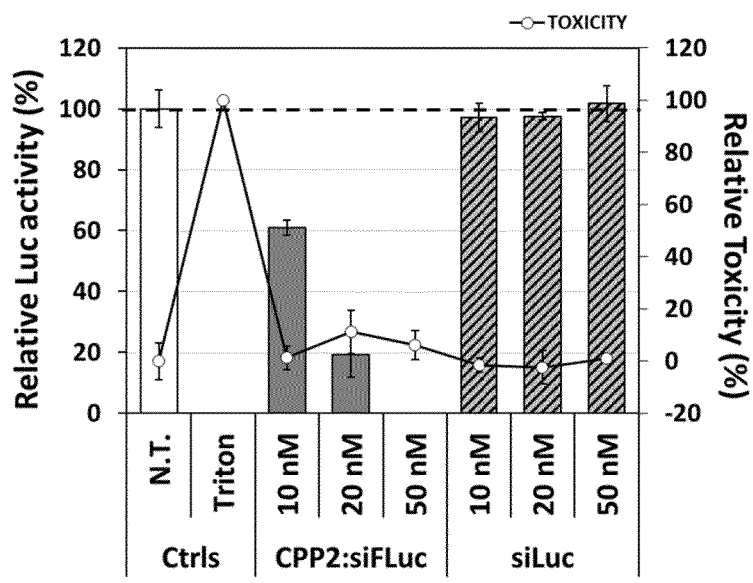
FIGURE 15 (Continue)

PEPTIDES FOR USE AS CELL-PENETRATING PEPTIDES

CROSS-REFERENCE TO RELATED APPLICATION

This application is the U.S. national stage application of International Patent Application No. PCT/EP2019/069149, filed Jul. 16, 2019.

The Sequence Listing for this application is labeled "Seq-List-replace.txt" which was created on Jan. 29, 2021 and is 5 KB. The entire content of the sequence listing is incorporated herein by reference in its entirety.

TECHNICAL FIELD

The present invention relates to non-naturally occurring peptides that may be used as cell-penetrating peptides. More particularly, the peptides of the invention are able to self-assemble with a cargo molecule, such as siRNA, to form peptide-based nanoparticles to transfect the cargo molecule into cells. The present invention also relates to pharmaceutical composition comprising said nanoparticles and a method for delivering cargo molecules into cells.

BACKGROUND

RNA interference (RNAi) in mammalian cells has opened unprecedented research opportunities to take advantage of this mechanism for treatment of various diseases. Short interfering RNAs (siRNAs) are double-stranded RNA molecules, with 20-25 base pairs in length including a 2-nucleotide overhang at each 3 prime end. The antisense strand of siRNA with sequence complementarity to a target mRNA can induce sequence-specific gene expression suppression (silencing). siRNA has been demonstrated to be a potential drug candidate for many difficult-to-treat diseases such as viral infections and cancers.

The design versatility and the highly specific nature of these oligonucleotides highlight their potential as drugs of the future. However, limitations such as the lack of cell penetration as well as the rapid endo/lysosomal degradation once inside the cell could be overcome by the use of specific carriers. A number of delivery technologies have been developed based on cationic lipids, polymers, dendrimers and peptides. Among these non-viral carrier materials, cell-penetrating peptides (CPP) have gained increasing popularity because of their sequence and function diversity. CPPs are usually short (up to 30 amino acids) peptides that originate from a wide variety of sources (e.g., humans, mice, viruses or purely synthetic). Based on their structural characteristics, CPPs can be divided into two classes: arginine-rich CPPs and amphipathic CPPs.

Amphipathic CPPs contain both hydrophilic and hydrophobic domains necessary for cellular internalization and interaction with the cargo. In primary amphipathic CPPs, these domains are distributed according to their position along the peptide chain as shown for pVEC (A. Elmquist et al. VE-Cadherin-Derived Cell-Penetrating Peptide, pVEC, with Carrier Functions, Exp. Cell Res. 269 (2001) 237-244), MPG and Pep-1 (S. Deshayes et al., (2005) Cell-penetrating peptides: tools for intracellular delivery of therapeutics, Cell. Mol. Life Sci. CMLS. 62, 1839-1849). Secondary amphipathic CPPs are another large class of peptides in which the separation between hydrophilic and hydrophobic domains occurs due to the secondary structure formation, such as α helices or β sheets. Many of the most commonly used CPPs are members of this class such as penetratin (D. Derossi et al., (1994) The third helix of the Antennapedia homeodomain translocates through biological membranes, J. Biol. Chem. 269(14) 10444-50), transportan (M. Pooga et al., (1998) Cell penetration by transportan, FASEB J. 12, 67-77), hCT-variants (human calcitonin) (J. Hoyer et al., (2012) Knock-down of a G protein-coupled receptor through efficient peptide-mediated siRNA delivery, J. Control. Release Off. J. Control. Release Soc. 161(3), 826-834), RICK (A. Vaissiére et al., (2017) A retro-inverso cell-penetrating peptide for siRNA delivery, J Nanobiotechnology. 15(1), 34) or C6M1 (M. Jafari et al., (2014) Serum stability and physicochemical characterization of a novel amphipathic peptide C6M1 for siRNA delivery, PLoS ONE. 9(5):e97797).

There are two main strategies to vectorize oligonucleotides using CPPs: by directly conjugating oligonucleotides to the CPPs (covalent conjugation approach) or by forming non-covalent complexes between the CPPs and oligonucleotides (nanoparticle-based approach). The formation of non-covalent nanoparticles (NPs) has been particularly efficient in the CPP-mediated delivery of oligonucleotides carrying multiple negative charges and therefore able to form electrostatic complexes with cationic peptides. In addition, formation of peptide-based nanoparticles is a one-step process very easy to perform since no chemical modification is required to allow NP assembly. Therefore, formation of electrostatic complexes remains the most popular application for CPP-mediated siRNA delivery.

However, up to now, the NP developed present some drawbacks, including lack of stability, few membrane permeability, few ability to silence in an efficient way the target gene, cytotoxicity, etc.

Thus, there still remains a need for improved cell-penetrating peptides that overcome the above-mentioned limitations. In particular, there is a need for cell-penetrating peptides enabling delivery of compounds such as therapeutic agents into target cells with high efficiency but without exerting significant cytotoxic and/or immunogenic effects.

SUMMARY OF THE INVENTION

By working on CPPs already developed and their deficiencies, the inventors have identified three essential amino acids that must be present at particular positions into the sequence to positively impact the solubility, secondary structure, low cytotoxicity and high uptake efficiency of the peptide. More particularly, the inventors have developed new CPPs composed exclusively of leucine (L), arginine (R) and tryptophan (W) residues, which overcome at least partially drawbacks of the previous CPPs. These new short amphiphilic peptides, also called WRAP, for W- and R-rich Amphipathic Peptides, might have tryptophan residues scattered all along the sequence or clustered in one domain of the sequence. Generally speaking, the peptides of the invention show a higher overall transfection efficacy, as well as a lower degree of cytotoxicity.

It is thus an object of the invention to provide a non-naturally occurring peptide comprising an amino acid sequence LL-[X]n-LL, wherein X is selected from R, L and W, and n=10 to 12, and wherein [X]n comprises 4 R, 4 L and 2 to 4 W.

In a particular embodiment, the peptide comprises an amino acid sequence LL-[X]m-RLL, wherein m=9 to 11.

In a particular embodiment, [X]n or [X]m comprises between 2 and 4 W, either clustered or scattered in the amino acid sequence.

Alternatively, or in addition, [X]n or [X]m may comprise at least one cluster consisting of LL, preferably two clusters consisting of LL.

In a particular embodiment, the peptide comprises or consists on the amino acid sequence selected from

```
                                    (SEQ ID No 1 - CPP1)
        LLWRLWRLLWRLWRLL, (SEQ ID No 2 - CPP2)
        LLRLLRWWWRLLRLL, (SEQ ID No 3 - CPP3)
        LLRLLRWWRLLRLL,
        and (SEQ ID No 4 - CPP4)
        LLRLLRWWWWRLLRLL
```

The peptides of the invention are particularly useful as cell-penetrating peptides (CPP). They are suitable to penetrate the plasma membrane of mammalian cells, as well as to be used as a transfection agent.

It is a further object of the invention to provide a nanoparticle comprising the peptide according to the invention and a cargo molecule. The cargo molecule may be selected from the group consisting of a nucleic acid, a peptide, a protein, a lipid, a small molecule, a pharmaceutically active agent, and mixture of any thereof. Advantageously, the cargo molecule is a nucleic acid, selected from the group consisting of DNA molecules, RNA molecules, PNA molecules, siRNA molecules, PMO molecules, antisense molecules, LNA molecules, mcDNA molecules, miRNA molecules, CRISPR/Cas9 molecules, plasmids, ribozymes, aptamers, spiegelmers and decoy molecules.

The nanoparticles of the invention may be used to manufacture a pharmaceutical composition. The present invention also provides a pharmaceutical composition comprising such, and a pharmaceutically acceptable carrier.

It is another object of the invention to provide a method for delivering cargo molecules into cells in vitro, and/or into tissues and/or organs ex vivo, comprising a step of putting said cells into contact with nanoparticles according to the invention, which comprises said cargo molecules.

The nanoparticles of the invention may also be used in a method for delivering cargo molecules in an animal, comprising a step of administrating of the nanoparticles of the invention to the animal, which comprises said cargo molecules.

For the surface representation two views are given to determine their amphipathic character: along the N-terminal to C-terminal axis and after a 90° turn. Tryptophan residues are given in red, arginine in blue and the others in yellow.

Figure 2:
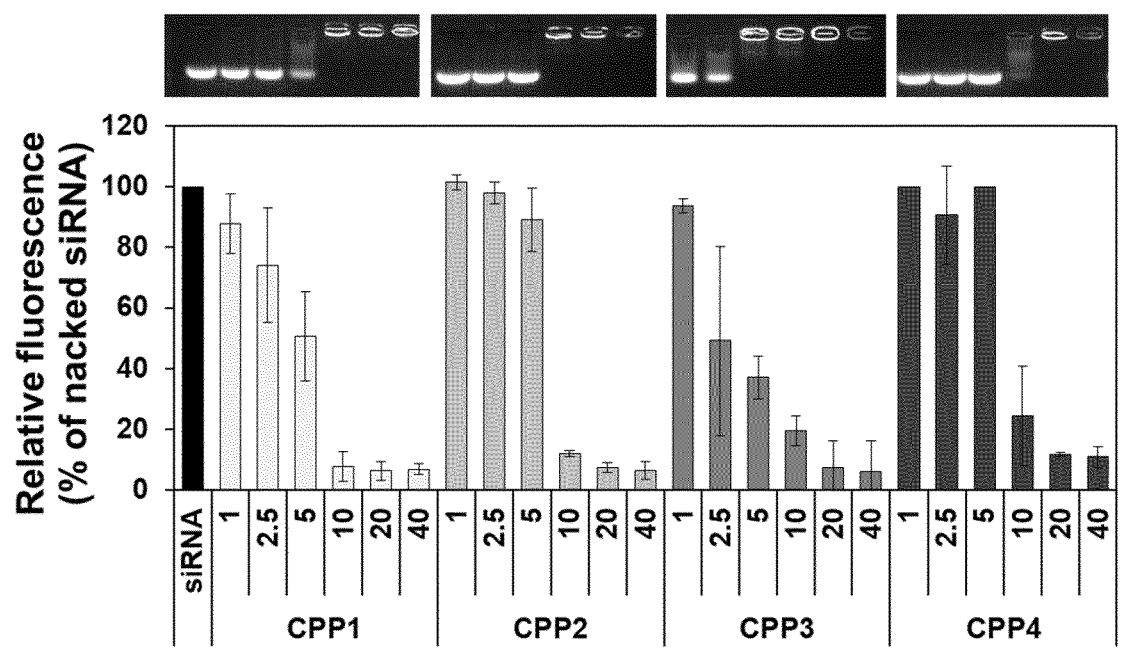
Figure 2:
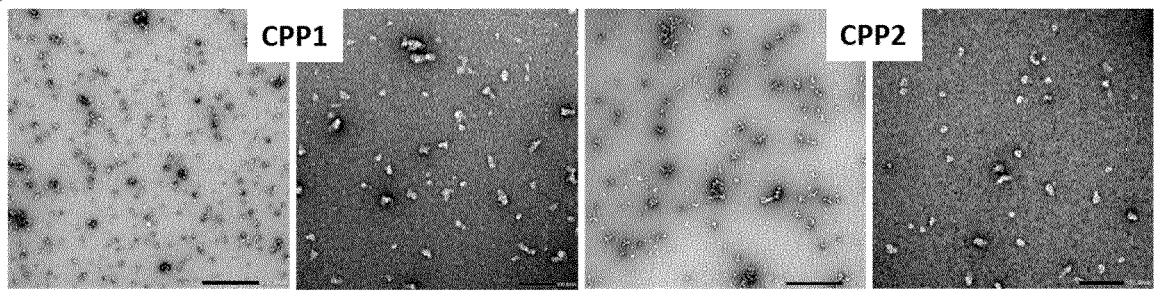

FIG. 2: Evaluation of the capacity of the amphipathic peptides to form complexes in the presence of siRNA. (A) Pre-formed CPP:siRNA complexes were analyzed by electrophoresis on agarose gel (1% wt/vol) stained with GelRed. Data represent: mean±SD, with n=3. (B) Transmission electronic microscopy (TEM) images of CPP1 and CPP2-based nanoparticle. Images of CPP:siRNA nanoparticles in ultrapure water (R=20, 40 µM CPP). Scales bars correspond to 500 nm and 100 nm for the magnified images.

Figure 3:
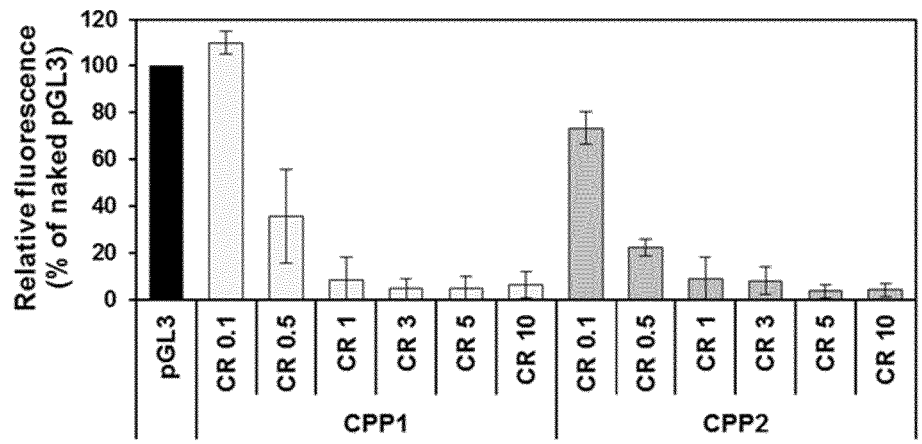
Figure 3:
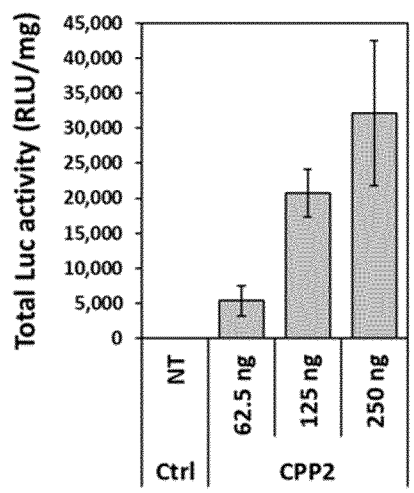
Figure 3:
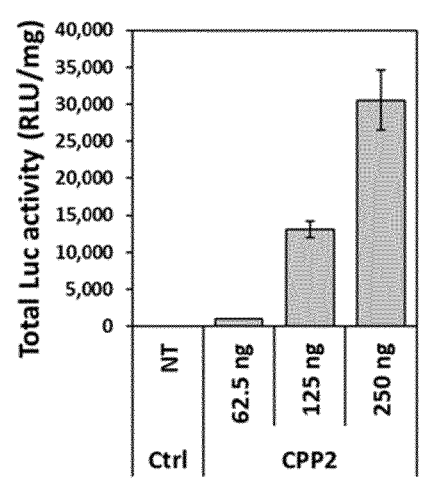

FIG. 3: Evaluation of the capacity of the amphipathic peptides to form complexes in the presence of plasmids. A) Graphical representation of the migration of the plasmid pre-formed CPP:pGL3 in an agarose gel. Pre-formed CPP:pGL3 complexes were formulated at different charge ratios (CR) and analyzed by electrophoresis on agarose gel (0.5% wt/vol) stained with GelRed. Data represent: mean±SD, with n=2. Dose-dependent expression of the luciferase after CPP2:pGL3 transfection in MEF cells (B) or in MCF-7 cells (C). Based on the gel migration properties of the CPP2:pGL3, nanoparticles were formulated at CR1 with three different plasmid concentrations (62.5 ng, 125 ng and 250 ng). NT=non-treated cells. Data represent: mean±SD, with n=2.

Figure 4:
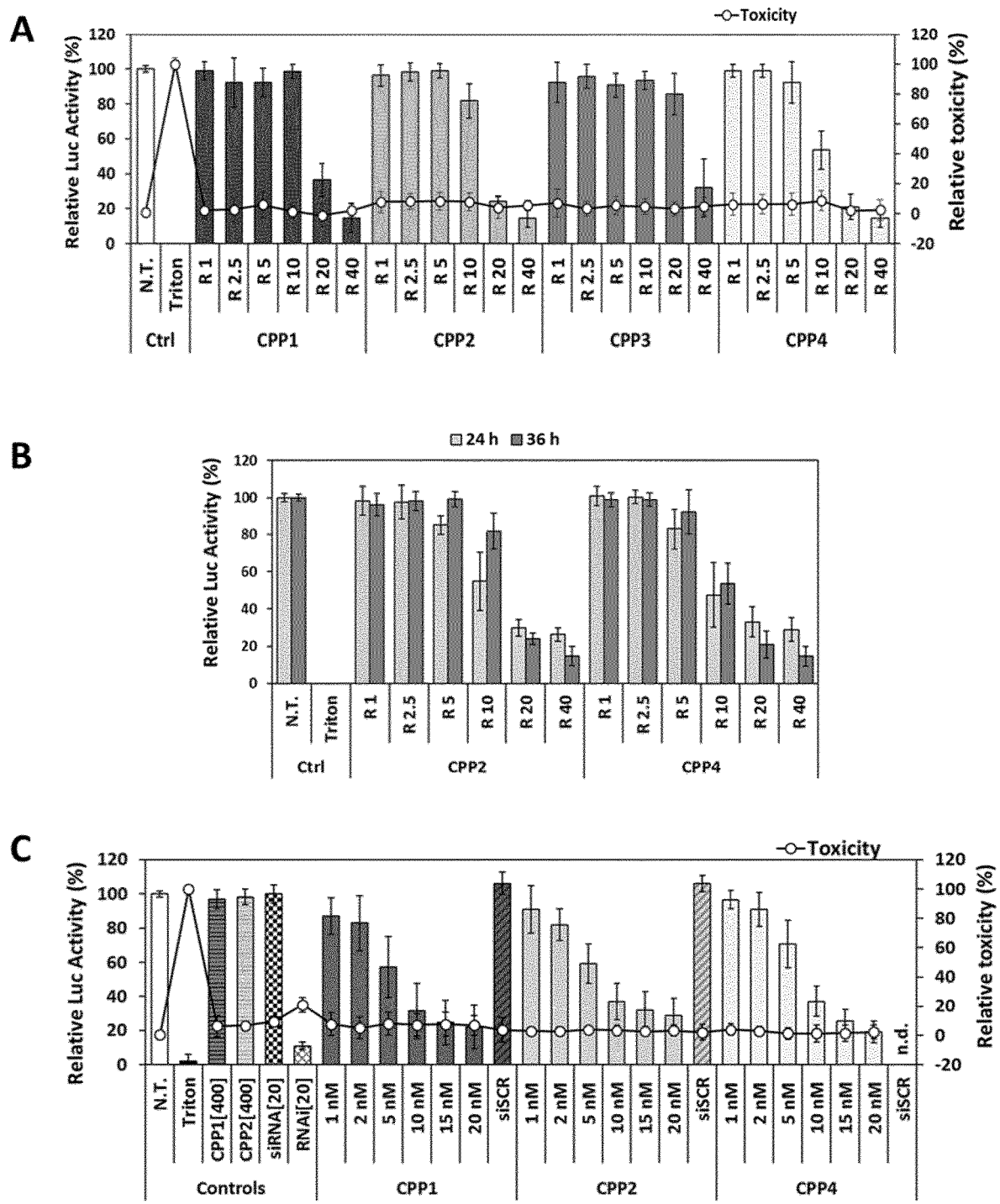

FIG. 4: Cellular evaluation of the knock-down efficiency CPP:siRNA nanoparticles. (A) Relative Luc activity (% FLuc/NLuc) and relative toxicity (LDH quantification) after transfection with CPP:siFLuc complexes in U87 cells at different molar ratios R at a constant siFLuc concentration of 20 nM. (B) Relative Luc activity (% FLuc/NLuc) depending on the total transfection time (24 h versus 36 h) on U87 cells. (C) Relative Luc activity (% FLuc/NLuc) and relative toxicity (LDH quantification) after transfection with CPP: siFLuc nanoparticles at different siFLuc concentrations on U87 cells (constant molar ration R=20). Lipofectamine® RNAiMAX is used as described by the supplier to transfect siFLuc at 20 nM (lane RNAi in the "Controls" panel). Abbreviations: R=molar ratio, siFLuc=siRNA FLuc, siSCR=scrambled siRNA, N.T.=non-treated cells, Ctrl=Controls, n.d.=not determined.

Figure 5:
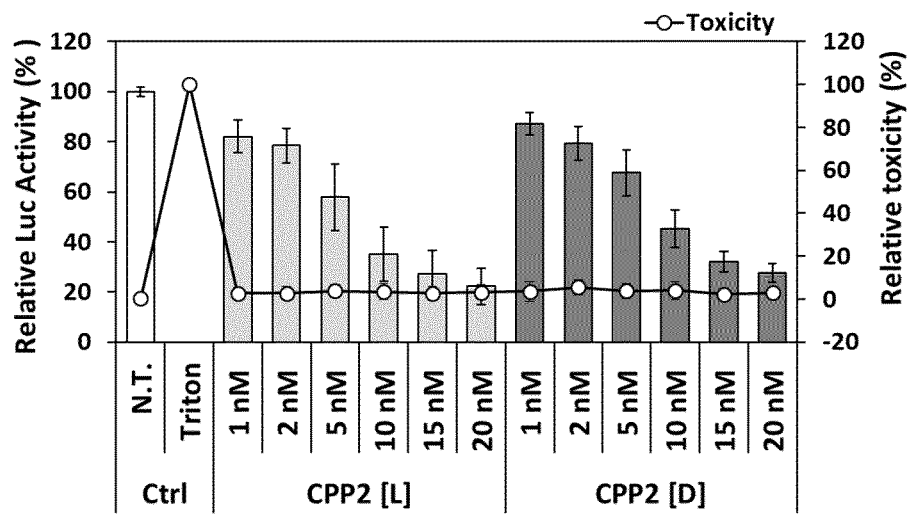

FIG. 5: Graphical representation of the reduction of expression of firefly luciferase depending on the concentration of the siRNA vectorized by CPP2 in isoform L (CPP2 [L]) or in isoform D (CPP2 [D]) on U87 cells. Normalization of FLuc/NLuc values to the condition of untreated cells (N.T.).

Figure 6:
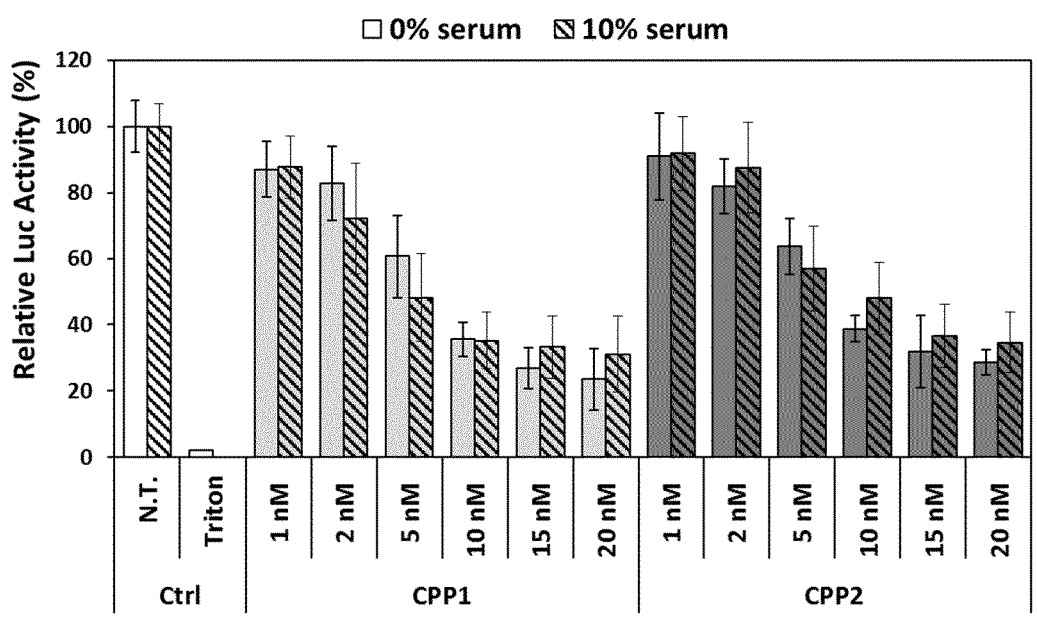

FIG. 6: Graphical representation of the firefly luciferase silencing depending on the concentration of the siRNA vectorized by CPP1 or CPP2. At all siRNA concentrations, the mode of delivery is effective even in the presence of 10% serum (U87 cells). Normalization of FLuc/Luc values to the condition of untreated cells (N.T.).

Figure 7:
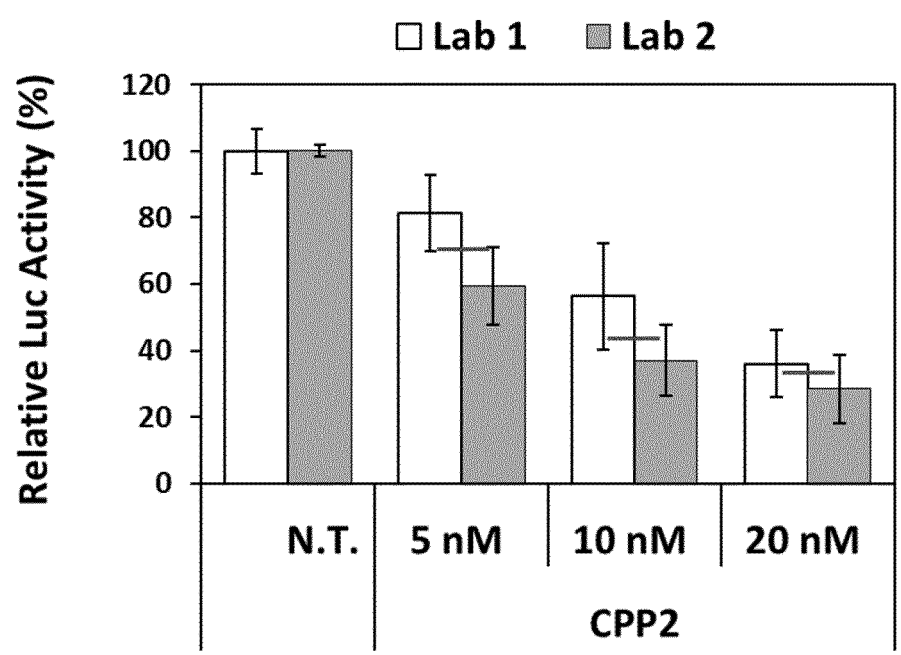

FIG. 7: Graphical representation of firefly luciferase expression reduction performed in different laboratories and with different reading methods (U87 cells). Normalization of FLuc/NLuc values to the condition of untreated cells (N.T.).

Figure 8:
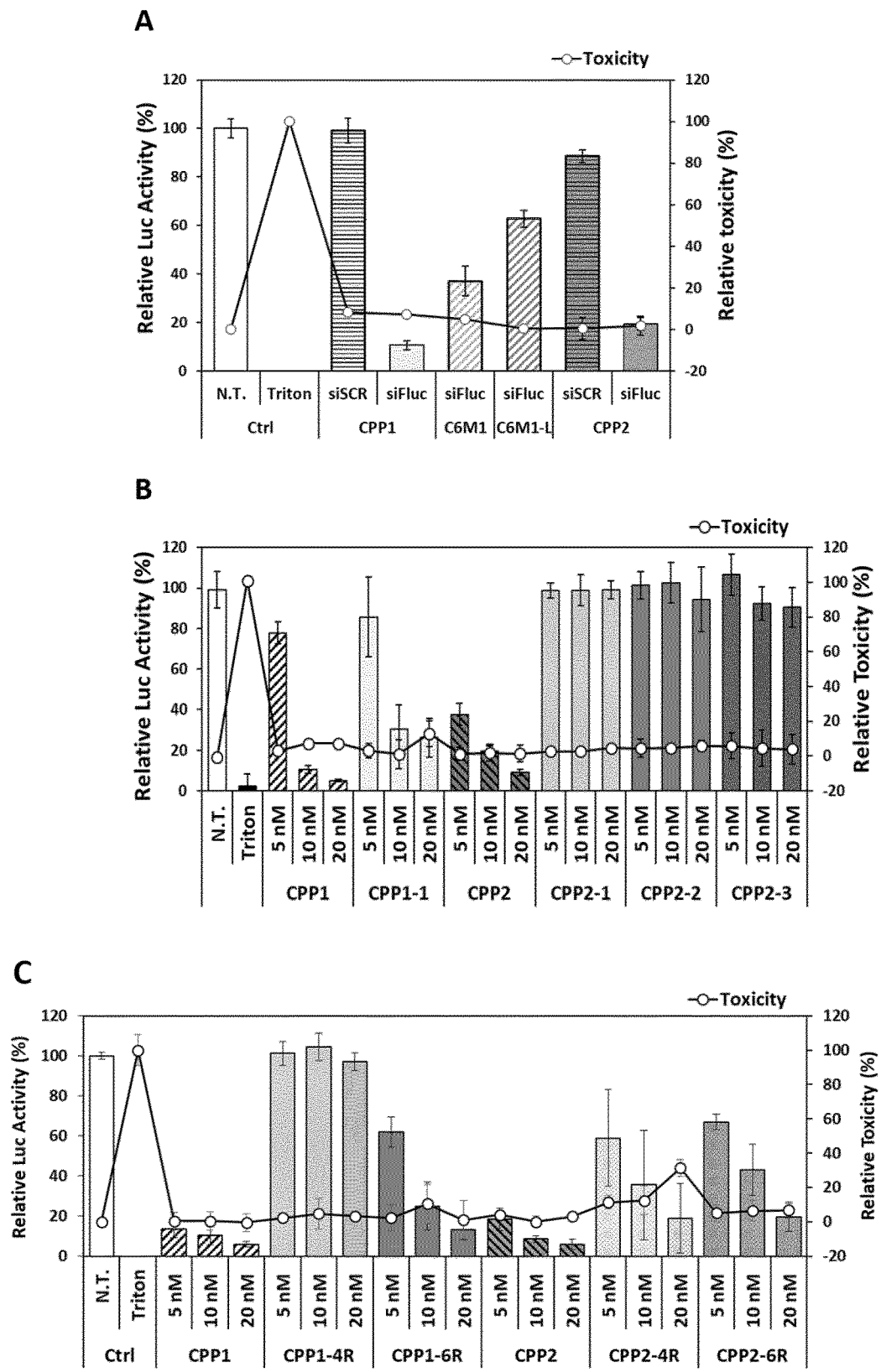

FIG. 8: Comparison of the CPP:siRNA with C6M1: siRNA or other derived CPPs. (A) Graphical representation of the knock-down efficiency of the firefly luciferase expression after CPP:siFluc transfection in U87 cells in comparison to C6M1:siFLuc. Incubation condition: 5,000 cells/well, nanoparticles with 200 nM peptide and 10 nM siRNA (vol:vol formulation), incubation time 1 h30. Normalization of FLuc/NLuc values to the condition of untreated cells (N.T.). n=2 independent experiments in triplicates. (B) Graphical representation of the knock-down efficiency of the firefly luciferase expression after CPP:siFluc transfection (vol:vol formulation) in U87 cells in comparison to derived CPP nanoparticles having mutations in the leucine "doublets" (see Table 1). Incubation condition: 5,000 cells/well, CPP:siRNA ratio=20:1 at the indicated siRNA concentration, incubation time 1 h30. Normalization of FLuc/NLuc values to the condition of untreated cells (N.T.). n=2 independent experiments in triplicates. (C) Graphical representation of the knock-down efficiency of the firefly luciferase expression after siFluc-loaded CPP:siFluc transfection (diluted formulation) in U87 cells in comparison to derived CPP2 nanoparticles having mutations (see Table 1). Incubation conditions: 5,000 cells/well, CPP:siRNA ratio=20:1 at the indicated siRNA concentration, incubation time 1 h30. Normalization of FLuc/NLuc values to the condition of untreated cells (N.T.). n=3 independent experiments in triplicates.

Figure 9:
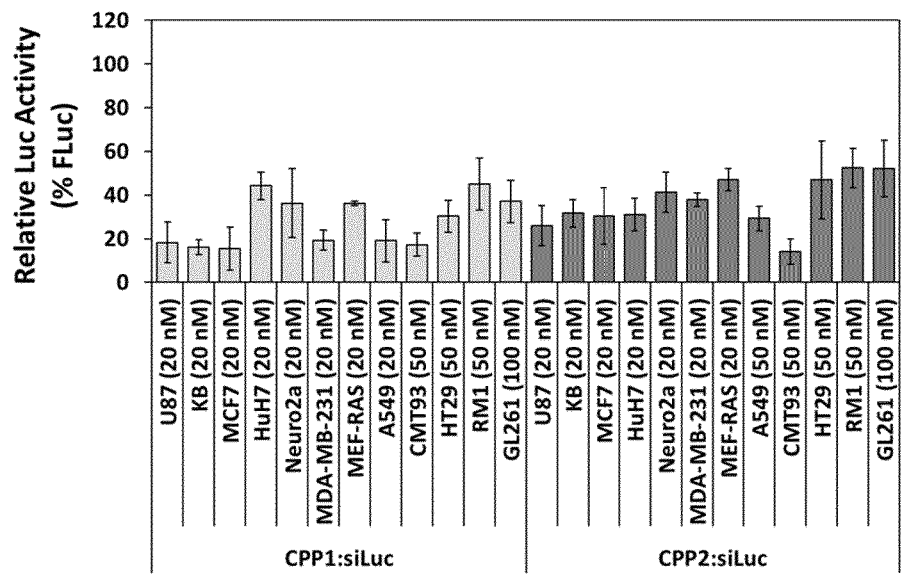
Figure 9:
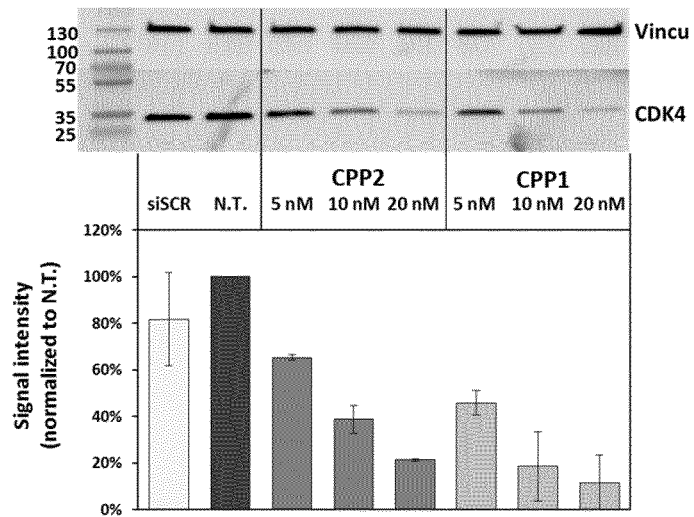

FIG. 9: Evaluation of CPP1:siRNA and CPP2:siRNA PBNs activity. (A) Relative FLuc activity (%) after CPP:siFLuc PBN transfection in different cell lines at the indicated siRNA-FLuc concentrations. U87: human gliomablastoma cell line, KB: keratin forming cell line derived from Hela, HuH7: human hepato carcinoma cell line, RM1: murine prostate carcinoma cell line, Neuro2a: murine neuroblastoma cell line, MCF7: human breast carcinoma cell line, MDA-MB-231: human breast adenocarcinoma, MEF-RAS: Ras-modified mouse embryonic fibroblasts, A549: adenocarcinomic human alveolar basal epithelial cells, HT29: human colon carcinoma cell line, CMT93: rectum carcinoma cell line, GL261: murine gliomablastoma cell line. (B) CDK4 silencing after CPP:siRNA nanoparticle transfection in U87 cells at the indicated siRNA-CDK4 concentrations. Abbreviations: siSCR=scrambled siRNA, N.T.=non-treated cells. (C) Comparison of the CPP1:siCDK4 nanoparticle activity with the activity of Lipofectamine® RNAiMAX as siRNA transfection agent on endogenous CDK4 protein expression in U87 cells. Black dashed line=no toxicity, red dashed line=dose-dependent toxicity. (D) Clonogenic assay for the evaluation cell cytotoxicity of the CPP2 nanoparticles compared to Lipofectamine® RNAiMAX. Different CPP2:siRNA nanoparticles (ratio 20, siRNA concentration 50 nM) were incubated on MEF-Ras cells (14 days) in comparison to the CPP2 peptide alone (100 nM) or to the RNAi:siRNA (siRNA concentration 20 nM) condition. (E) CDK4 silencing after CPP:siRNA nanoparticle transfection in U87 cells after a single dose of siCDK4 (20 nM), a double dose of siCDK4 (20 nM+20 nM) or a triple dose of siCDK4 (20 nM+20 nM+20 nM) after three days of culture. Abbreviations: siSCR=scrambled siRNA, N.T.=non-treated cells.

Figure 10:
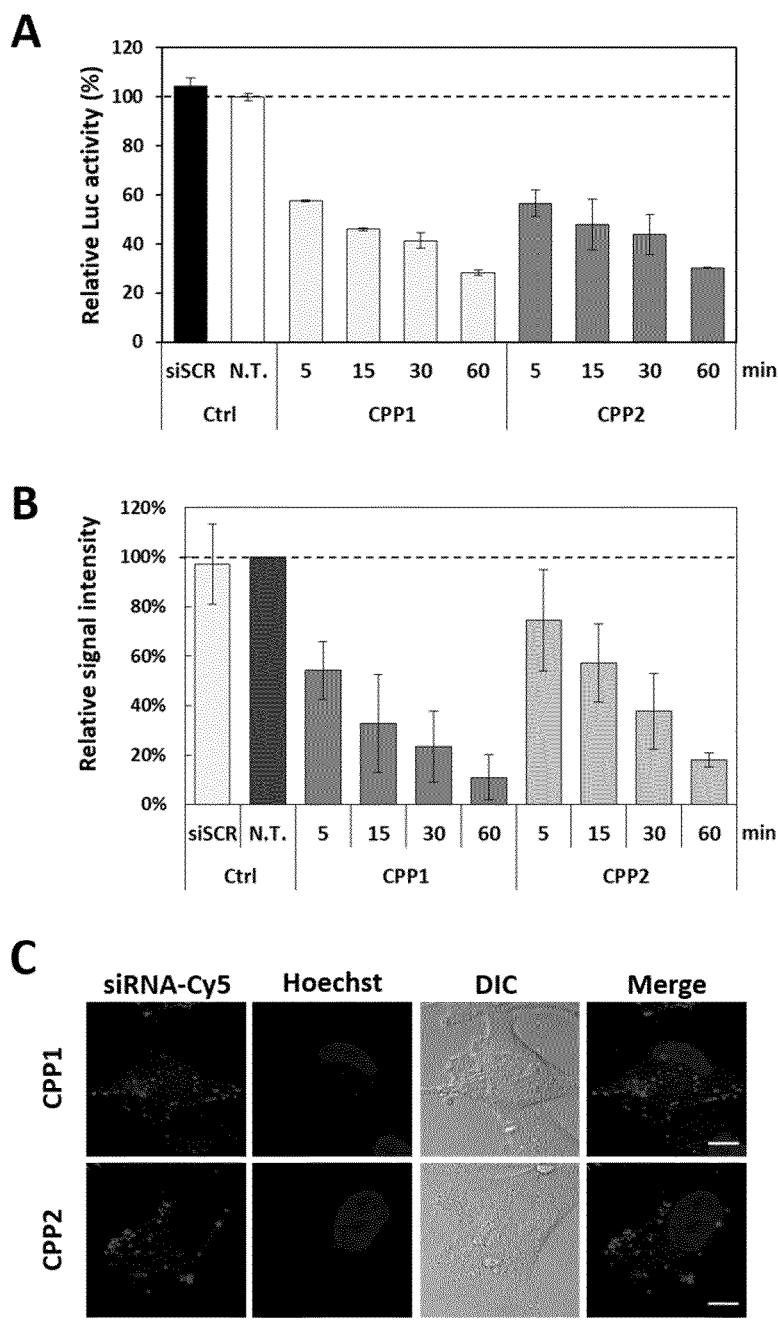
Figure 10:
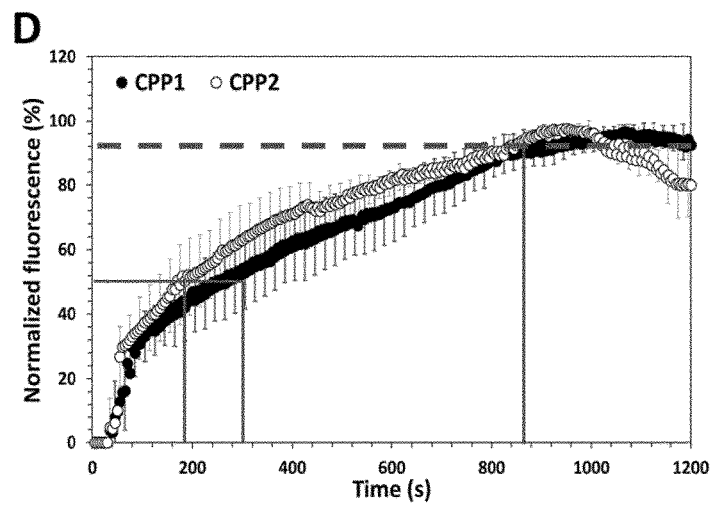

FIG. 10: Internalization kinetic of the CPPP:siRNA nanoparticles. (A) Relative FLuc activity (%) after CPP:siFLuc nanoparticle transfection in U87 cells at 20 nM siRNA-FLuc concentration for different incubation times in min. (B) CDK4 silencing after CPP:siRNA nanoparticle transfection in U87 cells at 20 nM siRNA-CDK4 concentration for different incubation times in min. (C) Visualization of cellular distribution of Cy5-labelled siRNA vectorized by CPP1 or CPP2 nanoparticles (siRNA-Cy5=20 nM, R=20) in living U87 cell line. Nuclei were labeled using Hoechst 33342 dye. White bars represent 20 μm. (D) Comparison of CPP1:siRNA-Cy3b and CPP2:siRNA-Cy3b internalization kinetic by spinning disk (siRNA-Cy3b=20 nM, R=20) with image recorded every 5 s for 1200 s. Thereafter, the percentage of mean grey values was plotted against the time (mean±SD; 2-5 individual counted cells from 2 to 3 independent experiments).

Figure 11:
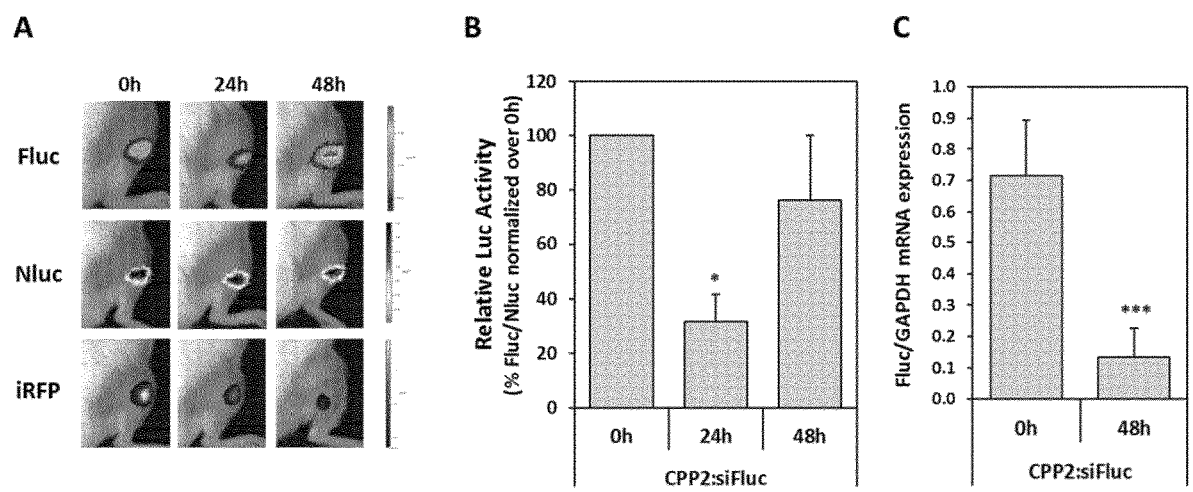

FIG. 11: Nanoparticles induced a reduction in firefly luciferase expression in vivo on a tumor model of xenografted mouse. (A) Representative image of dual bioluminescence (Fluc and Nluc) and tumor fluorescence (U87-CMV-Fluc-CMV-iRFP-IRES) at the indicated time post-injection of CPP2 nanoparticles: siFluc. (B) Quantitative analysis of Fluc and Nluc luciferases directly after intratumoral injection of nanoparticles: siFluc (15 μg of siRNA). Statistical analysis (mean±SEM, n=11): one-way ANOVA versus 0 h (=control) with a Dunnet post-test, *p<0.05. (C) Quantitative analysis of Fluc mRNA directly after intratumoral injection of CPP2 nanoparticles: siFluc (20 μg of siRNA). Statistical analysis (mean±SD, n=4): t-test versus 0 h (=control), ***p=0.0009. The Fluc mRNA level is expressed as a ratio to the mRNA of the GAPDH protein (Fluc/GAPDH).

Figure 12:
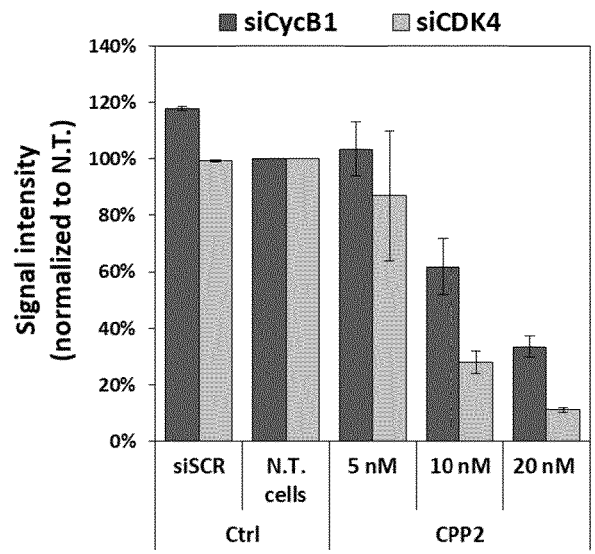
Figure 12:
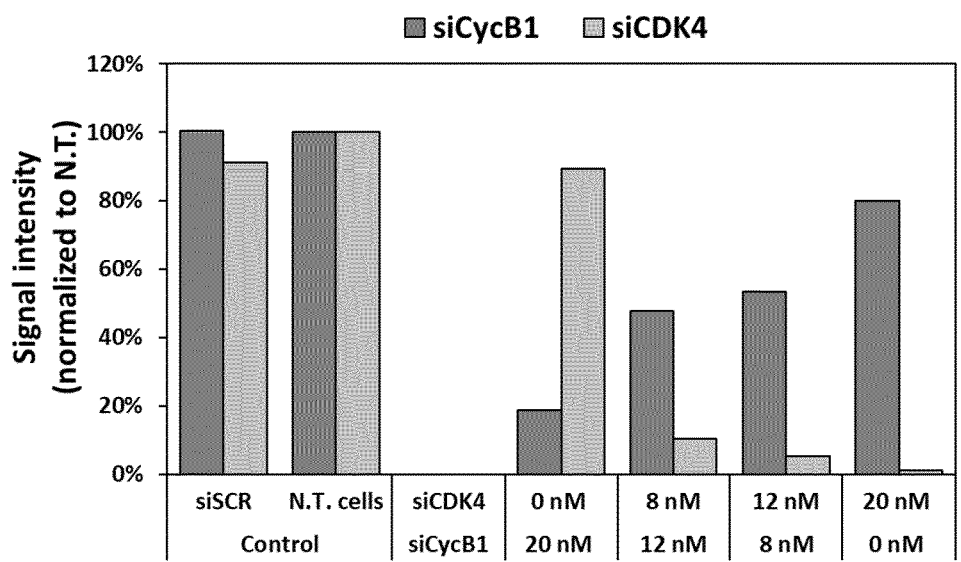

FIG. 12: Vectorization of siRNA cocktails by the CPP nanoparticles. (A) Simultaneous transfection of 2 siRNAs by PBNs: The [CPP2:siCDK4/siCycB1] mixture shows a dose-dependent reduction in expression of the endogenous CDK4 and Cyclin B1 proteins in U87 cells. (B) Transfection by the PBNs of 2 siRNAs at different stoichiometries: The [CPP1:siCDK4/siCycB1] mixture shows a reduction in expression of endogenous CDK4 and Cyclin B1 (U87 cells) proteins inversely proportional to the content of each of the siRNAs.

Figure 13:
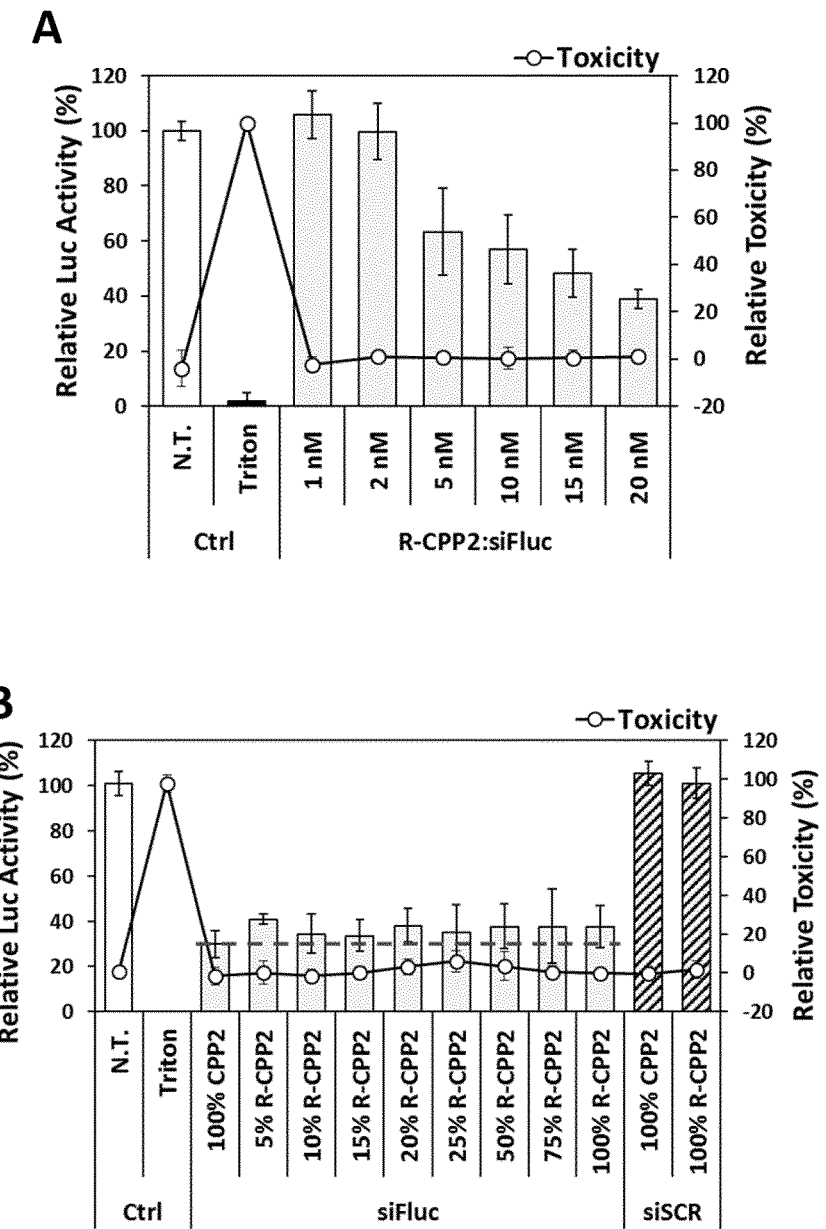
Figure 13:
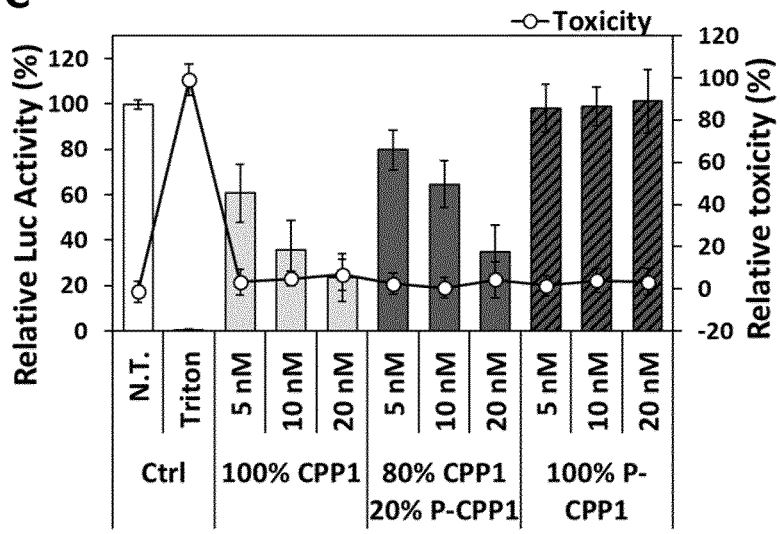
Figure 13:
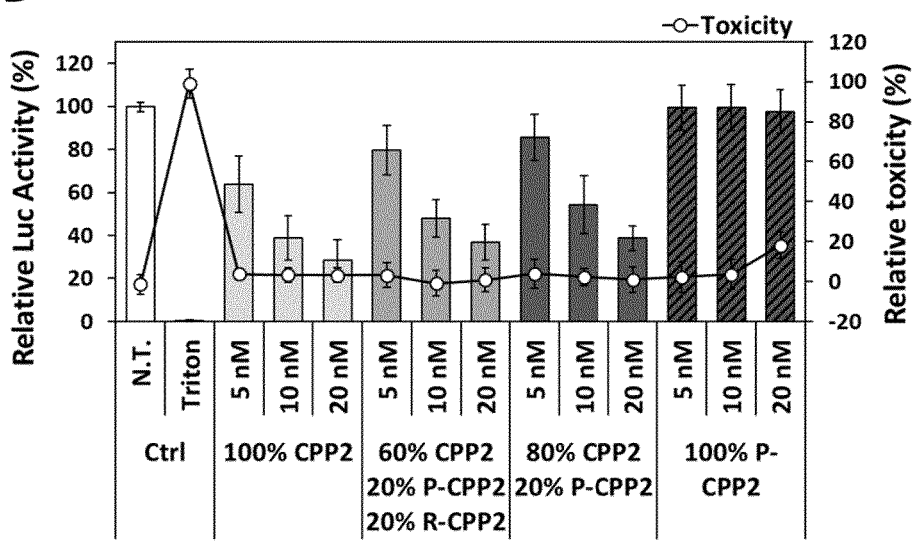
Figure 13:
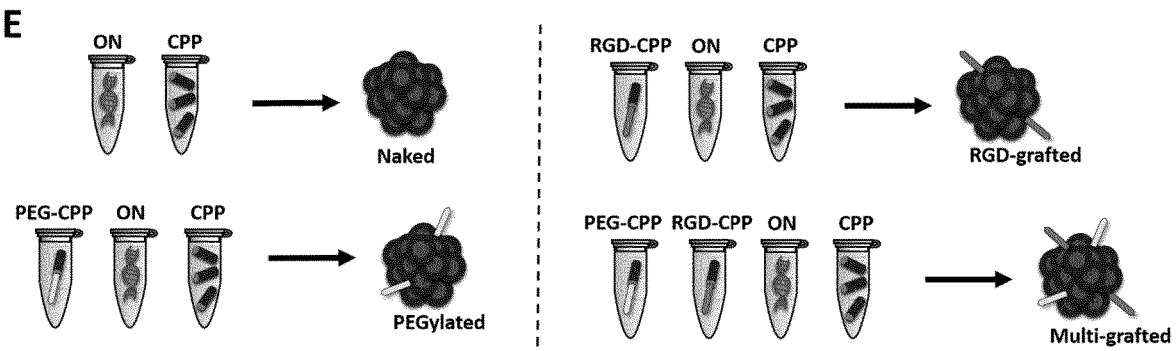

FIG. 13: Development of multi-grafted nanoparticles. (A) Relative FLuc activity (%) after siFluc transfection by RGD-Ahx-CPP2 peptide (R-CPP2, R=20) in a dose-dependent manner. (B) CPP2: RGD-Ahx-CPPs mixtures (CPP2:R-CPP2 ratio from 100%:0% to 0%:100%) did not influence the silencing of Fluc luciferase activity (R=20 with 20 nM siFluc). (C) Influence of PEGylation rate of CPP1 nanoparticles on the activity of Fluc luciferase (R=20 with 20 nM siFluc). (D) Influence multi-grafted CPP2 nanoparticles on the activity of Fluc luciferase (R=20 with 20 nM siFluc). (E) Schematic representation of peptide nanoparticles made by simple mixtures of different entities.

Figure 14:
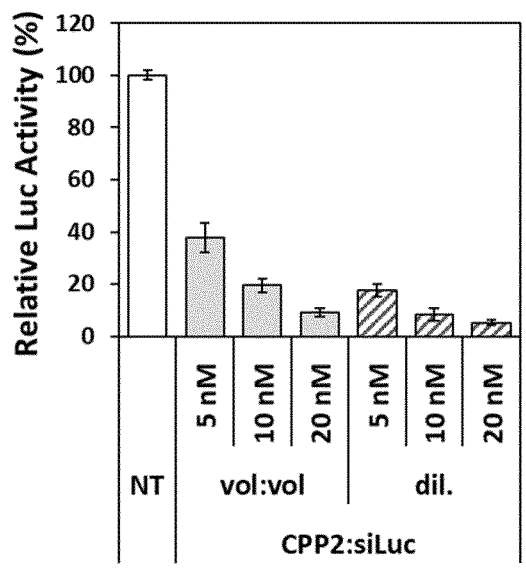

FIG. 14: Graphical representation of the firefly luciferase silencing in U87 cells depending on the applied formulation conditions. U87 cells were seeded in a P96 well plate (5,000 cellules/well). Nanoparticles were formulated using the "vol:vol" condition (final concentrations CPP:siRNA 100 nM:5 nM; 200 nM:10 nM and 400 nM:20 nM) or at high concentration (CPP[10 μM]:siRNA[0.5 μM]) followed by a dilution (="dilution" condition). Incubation time of the nanoparticles was 1 h30 in serum-free medium. After the addition of serum, the cells were incubated 36 h before performing the luciferase assay. Normalization of FLuc/NLuc values to the condition of untreated cells (N.T.). n=2 independent experiments in triplicates.

Figure 15:
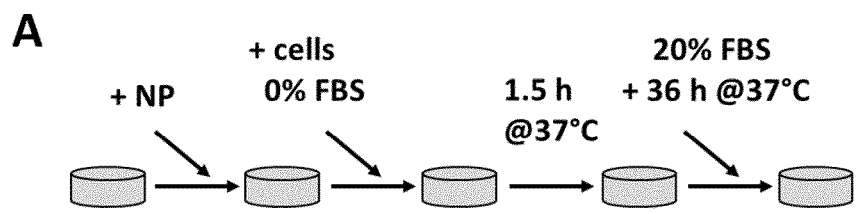
Figure 15:
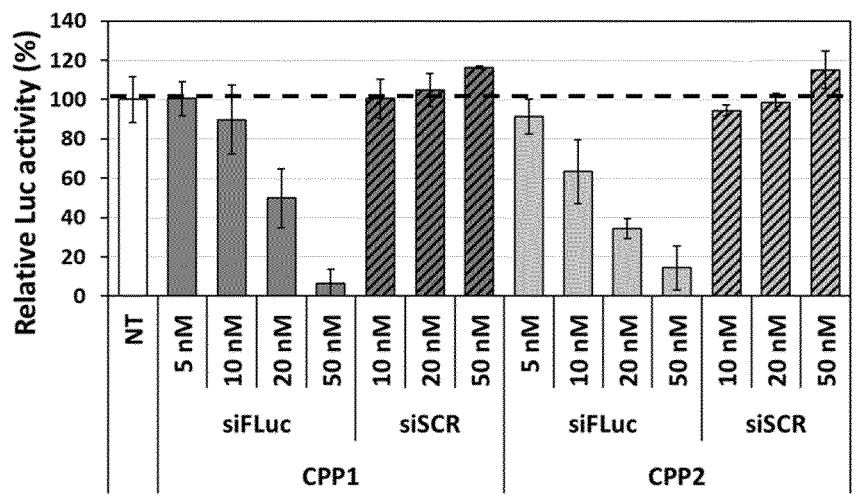

FIG. 15: Evaluation of CPP1:siRNA and CPP2:siRNA PBNs activity on cell suspensions. (A) Relative FLuc activity (%) after CPP:siFLuc nanoparticle transfection in U87 cell suspensions in a dose-dependent manner (siRNA=10 nM, 20 nM and 50 nM). Incubation conditions: 10,000 cells/well, CPP:siRNA ratio=20:1 at the indicated siRNA concentration, incubation time 1.5 h in serum-free medium. Normalization of FLuc/NLuc values to the condition of untreated cells (N.T.). Abbreviations: siSCR=scrambled siRNA, siFLuc=firefly luciferase specific siRNA. n=2 independent experiments in triplicates. (B) Relative FLuc activity (%) after CPP:siFLuc nanoparticle transfection in U87 cell suspensions in a dose-dependent manner (siRNA=10 nM, 20 nM and 50 nM). Incubation conditions: 10,000 cells/well, CPP:siRNA ratio=20:1 at the indicated siRNA concentration, incubation time 1.5 h in medium containing 10% serum. Normalization of FLuc/NLuc values to the condition of untreated cells (N.T.). Abbreviations: siSCR=scrambled siRNA, siFLuc=firefly luciferase specific siRNA. n=2 independent experiments in triplicates. (C) Relative FLuc activity (%) after CPP:siFLuc nanoparticle transfection in firefly luciferase stable transfected U937 human macrophage suspension in a dose-dependent manner (siRNA=10 nM, 20 nM and 50 nM). Incubation conditions: 10,000 cells/well, CPP:siRNA ratio=20:1 at the indicated siRNA concentration (or the siRNA alone), incubation time 1.5 h in serum-free medium. Normalization of FLuc values to the condition of untreated cells (N.T.). n=2 independent experiments in triplicates.

Figure 16:
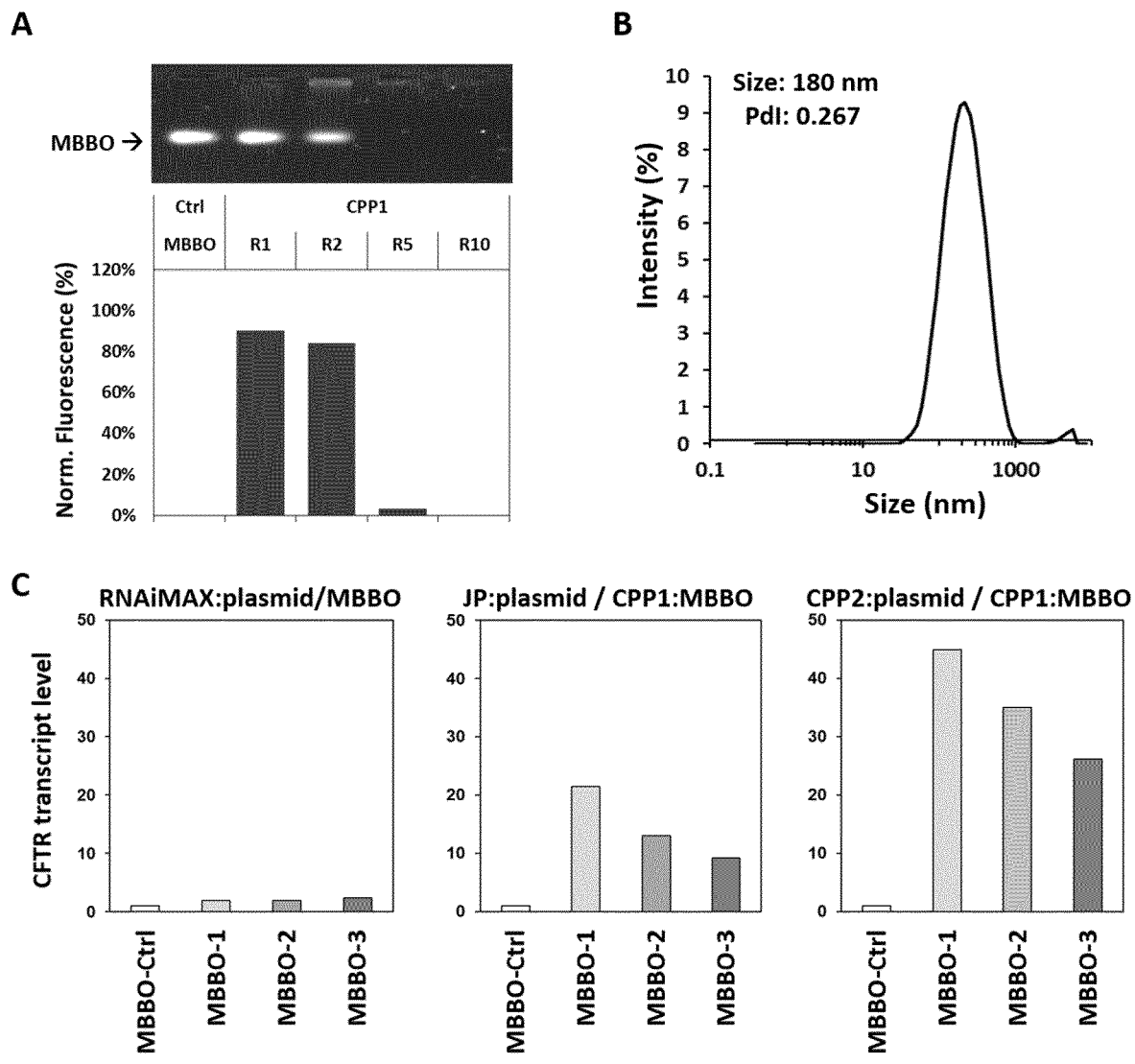

FIG. 16: Evaluation of MBBO and plasmid co-transfection in the context of cystic fibrosis. (A) Pre-formed CPP1:MBBO complexes were analyzed by electrophoresis on agarose gel (1% wt/vol) stained with GelRed. Data represent: mean±SD, with n=2. (B) Measurement of the mean size of the CPP1:MBBO complexes (R=5, 10 μM CPP1) by dynamic light scattering (DLS). (C) Bronchial Beas-2b cells were transfected with 1 μg CFTR-encoding plasmid using Lipofectamin™ RNAiMAX, JetPei® (PJ) or CPP2 and with 100 nM MBBO using RNAiMAX or CPP1. Amount of CFTR transcript and of the house-keeping gene GAPDH was determine by qPCR. The CFTR values were first normalized to GAPDH and then to the control condition using a MBBO with no 3'-UTR binding property (MBBO-Ctrl=1).

DETAILED DESCRIPTION OF THE INVENTION

Definitions

The terms "peptide" or "peptide molecule", as used herein, refer to any naturally occurring or non-naturally occurring (e.g., generated by chemical synthesis or recombinant DNA technology) linear macromolecules comprising a plurality of natural or modified amino acid residues connected via peptide bonds.

The term "amino acid residue", as used herein, denotes any of the 20 "standard" amino acids that are naturally incorporated into peptides. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G:

glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr). Typically, the amino acid residues of a peptide according to the invention are present as L-isomers or D-isomers. The term "non-natural amino acid residue", as used herein, denotes non-coded or non-proteinogenic amino acids are those not naturally encoded or found in the genetic code of any organism. The term "modified amino acid residue", as used herein, denotes non-standard amino acids such as post-translationally modified amino acids. Examples of post-translational modifications include phosphorylation, glycosylation, acylation (e.g., acetylation, myristoylation, palmitoylation), alkylation, carboxylation, hydroxylation, glycation, biotinylation, ubiquitinylation, changes of the chemical nature (e.g., β-elimination deimidation, deamidation), and structural changes (e.g., the forming of disulfide bridges).

Cell Penetrating Peptides

The present invention refers to new non-naturally occurring peptides comprising the amino acid sequence LL-[X]n-LL, wherein X is selected from R, L and W, and n=10 to 12, and wherein [X]n comprises 4 R, 4 L and 2 to 4 W, preferably 3 to 4 W.

The present inventors have surprisingly found that such peptides, which are referred to herein as the peptides according to the invention, are suitable to act as cell-penetrating peptides (CPP) and may thus deliver cargo molecules to the cytoplasm of a cell, preferably through the plasma membrane of mammalian cells.

The peptides of the invention have a length between 14 and 16 amino acid residues, all selected from R, L and W. Indeed, the inventors have discovered that particular distributions of such three amino acid residues into the amino acid sequence of the peptide lead to peptides of particular interest as CPP. Indeed, said peptides show high cellular uptake ability, non-significant cytotoxic and/or immunogenic effects to their respective target cells after having been internalized (i.e., they do not interfere with cell viability, at least at concentrations that are sufficient to mediate cellular transfection and/or penetration). The term "non-significant", as used herein, is to be understood that less than 30%, and particularly less than 20% or 10% of the target cells are killed after internalization of a peptide of the invention. The skilled person is well aware of methods of determining the cytotoxicity of a given compound and/or the viability of a given target cell to which such a compound is applied (see also, e.g., Ausubel, F. M. et al. (2001) Current Protocols in Molecular Biology, Wiley & Sons, Hoboken, N.J., USA).

The term "cellular uptake ability", as used herein, refers to the ability of the peptides to pass cellular membranes (i.e., plasma membrane), endosomal membranes, and membranes of the endoplasmic reticulum) and/or to direct the passage of a given cargo molecule through these cellular membranes (i.e. its transfection capability). The peptides having said ability to pass through cellular membranes are herein referred to as "cell-penetrating peptides" or "CPP". Numerous methods of determining the internalization behavior and/or transfection capability of a given peptide are established in the art, for example, by attaching a detectable label (e.g. a fluorescent dye) to the peptide (and/or to the cargo molecule to be transfected) or by fusing the peptide with a reporter molecule, thus enabling detection once cellular uptake of the peptide occurred, e.g., by means of FACS analysis or via specific antibodies (see, e.g., Ausubel, F. M. et al. (2001) Current Protocols in Molecular Biology, Wiley & Sons, Hoboken, N.J., USA). The skilled person is also well aware how to select the respective concentration ranges of the peptide and, if applicable, of the cargo to be employed in such methods, which may depend on the nature of the peptide, the size of the cargo, the cell type used, and the like.

In a particular embodiment, the peptide of the invention comprises the amino acid sequence LL-[X]m-RLL, wherein m=9 to 11.

Advantageously, [X]n or [X]m comprises a cluster consisting of WW, WWW or WWWW. Preferably, such cluster is central, that is to say that there is the same number of amino acid residues from each side of the tryptophan cluster.

In a particular embodiment, [X]n or [X]m comprises at least one cluster consisting of LL, preferably two clusters consisting of LL.

Advantageously, the peptide of the invention has a net-positive charge of 5.

In a particular embodiment, the peptide comprises or consists on the amino acid sequence selected from LLWRLWRLLWRLWRLL, (SEQ ID No 1)

LLRLLRWWWRLLRLL, (SEQ ID No 2)

-continued

LLRLLRWWRLLRLL, (SEQ ID No 3)
and

LLRLLRWWWWRLLRLL. (SEQ ID No 4)

In a particular embodiment, the peptide further comprises covalently linked to the C-terminal end of said amino acid sequence, one or several entities chosen amongst a L-amino acid, a D-amino acid, a non-natural amino acid, a modified amino acid, a cysteamide, a thiol, an amide, a carboxyl, a linear or ramified $C_1$-$C_6$ alkyl optionally substituted, a primary or secondary amine, an osidic derivative, a lipid, a phospholipid, a fatty acid, a cholesterol, a poly-ethylene glycol, a nuclear localization signal, and/or a targeting molecule, and/or wherein the peptide further comprises covalently linked to the N-terminal end of said amino acid sequence, one or several chemical entities chosen amongst a L-amino acid, a D-amino acid, a non-natural amino acid, a modified amino acid, an amine, an acetyl, a linear or ramified $C_1$-$C_6$ alkyl optionally substituted, a primary or secondary amine, an osidic derivative, a lipid, a phospholipid, a fatty acid, a cholesterol, a poly-ethylene glycol, a nuclear localization signal, and/or a targeting molecule.

Nanoparticles

The present invention further provides nanoparticles, comprising at least one peptide according to the invention, complexed with at least one cargo molecule. Such cargo molecule may be any cargo molecule as defined herein. According to a particular embodiment, the nanoparticle may comprise more than one peptide according to the present invention. Particularly, the nanoparticle may comprise a plurality of the same or of different peptides. Also, the nanoparticle may comprise more than one cargo molecule. Particularly, the nanoparticle may comprise a plurality of the same or of different cargo molecules.

Advantageously, the size of the nanoparticle is between 50 and 300 nm, preferably between 100 and 200 nm.

In one embodiment, the complex between the peptide(s) and cargo molecule(s) can be formed based on non-covalent bond(s). Such non-covalent bonds can be ionic bonds, hydrogen bonds or hydrophobic interactions or a combination of such bonds.

Alternatively, the complex between the peptide(s) and the cargo molecule(s) is formed by covalent bonds. Such covalent bonds are preferably formed between either a suitable reactive group of the peptide and the cargo and more preferable between a terminus of the peptide according to the present invention and the cargo molecule(s). Depending on the chemical nature or the cargo molecules, the moiety, group or radical with which such covalent bond is formed varies and it is within the skills of a person of the art to create such bond.

Advantageously, the cargo molecule is selected from the group consisting of a nucleic acid, a peptide, a protein, a lipid, a small molecule, a pharmaceutically active agent, and mixture of any thereof.

The peptides of the invention are particularly suited for complexing with nucleic acid molecules. It is thus a particular object of the present invention to provide nanoparticles comprising a peptide of the invention and a nucleic acid molecule, or mixture of any thereof, selected from the group consisting of DNA molecules, RNA molecules, PNA molecules, siRNA molecules, PMO molecules, antisense molecules, LNA molecules, mcDNA molecules, miRNA molecules, CRISPR/Cas9 molecules, plasmids, ribozymes, aptamers, spiegelmers and decoy molecules.

The term "miRNA molecule" (or "miRNA"), as used herein, refers to an endogenous RNA molecule derived from a genomic locus that is processed from transcripts that can form local RNA precursor miRNA structures. The mature miRNA is usually 20, 21, 22, 23, 24, or 25 nucleotides in length, although other numbers of nucleotides may be present as well, for example 18, 19, 26 or 27 nucleotides.

The term "shRNA molecule" (i.e. short hairpin RNA molecule), as used herein, refers to an artificial single-stranded interfering RNA molecule comprising both sense and anti-sense strand of a "siRNA duplex" in a stem-loop or hairpin structure. The stem of this hairpin structure typically ranges from 19 to 29 nucleotides in length, and a loop typically ranges from 4 to 15 nucleotides in length.

The term "siRNA molecule" refers to a small interfering RNA directed to a target nucleic acid, preferably mRNA, coding for the target molecule. siRNA is a double stranded RNA having typically a length of about 21 to 23 nucleotides. The sequence of one of the two RNA strands corresponds to the sequence of the target nucleic acid to be degraded. Thus, knowing the nucleic acid sequence of the target molecule, preferably the mRNA sequence, a double stranded RNA may be designed with one of the two strands being complementary to said mRNA of the target molecule and, upon application of said siRNA to a system containing the gene, the respective corresponding target nucleic acid will be degraded and thus the level of the respective protein be reduced.

The term "Ribozyme" refers to a catalytically active nucleic acid, which preferably consists of RNA which basically comprises two moieties. The first moiety shows a catalytic activity, whereas the second moiety is responsible for the specific interaction with the target nucleic acid.

The term "Aptamer" refers to a D-nucleic acid, which is either single stranded or double stranded and which specifically interacts with a target molecule. Aptamers are currently used as therapeutic agents.

The term "Spiegelmers" refers to L-nucleic acids, i.e., composed of L-nucleotides. Spiegelmers are characterized by the fact that they have a very high stability in biological system and, comparable to aptamers, specifically interact with the target molecule against which they are directed.

In another embodiment the cargo molecule is a peptide, consisting of at least two amino acids which are covalently linked, preferably through a peptide bond. In an embodiment the peptide consists of L-amino acids, D-amino acids, non-natural amino acids or mixtures thereof.

Alternatively, the cargo molecule is a protein.

In another embodiment, the cargo molecule is a small molecule, preferably having a molecular weight of 1,000 Da or less. Particularly, the small molecule is a drug or a drug candidate.

In another embodiment, the cargo molecule is a pharmaceutically active agent.

In another embodiment, the cargo molecule is a lipid.

In another embodiment, the cargo molecule is an antibody or a protein.

Pharmaceutical Composition

It is a further object of the invention to provide a pharmaceutical composition comprising nanoparticles of the invention (i.e. at least one peptide attached to at least one cargo molecule) and one or more pharmaceutically acceptable carrier. Indeed, the nanoparticles of the present invention may be advantageously used to manufacture a pharmaceutical composition.

The term "pharmaceutical composition", as used herein, relates to a composition for administration to a subject, preferably to a human patient. Pharmaceutical compositions according to the present invention include any pharmaceutical dosage forms established in the art, such as capsules, microcapsules, cachets, pills, tablets, powders, pellets, multi-particulate formulations (e.g., beads, granules or crystals), aerosols, sprays, foams, solutions, dispersions, tinctures, syrups, elixirs, suspensions, water-in-oil emulsions such as ointments, and oil-in water emulsions such as creams, lotions, balms, skin patches, drops, pastes and suppositories.

The pharmaceutical compositions of the invention include formulations suitable for oral, rectal, nasal, topical (including buccal and sub-lingual), peritoneal and parenteral (including intramuscular, subcutaneous and intravenous) administration, or for administration by inhalation or insufflation. Administration may be local or systemic.

Another aspect of the present invention is the use of a nanoparticle as above-described, as a medicament and as a marker or an imaging agent.

The present invention also pertains to a method for delivering a molecule into a cell in vitro, comprising a step of putting said cell into contact with a nanoparticle or pharmaceutical composition as described above. The present invention also pertains to a method for delivering a molecule into tissues and/or organs ex vivo, comprising a step of putting said tissues and/or organs into contact with a nanoparticle or pharmaceutical composition as described above.

The present invention method for delivering cargo molecules in vivo, comprising a step of administration of said animals into contact with nanoparticles according to any of claims 13 to 17, which comprises said cargo molecules Several aspects of the present invention are further developed in the following examples, illustrated by the figures (which are described in the examples).

Examples

Material & Methods

Materials. Dioleylphosphatidylglycerol (DOPG) and dioleylphosphatidylcholine (DOPC) phospholipids, cholesterol (Chol), sphingomyelin (SM) were purchased from Avanti Polar Lipids. Large Unilamellar Vesicles (LUVs) were prepared by the extrusion method from a lipid mixture of DOPC/SM/Chol (2:2:1) as previously reported (A. Vaissière et al., (2017) A retro-inverso cell-penetrating peptide for siRNA delivery, J Nanobiotechnology. 15(1), 34).

The different siRNA sequences (unlabeled and Cy5-labeled) were purchase are form Eurogentec. Cy3b-labeled siRNA was purchase from BioSynthesis. The following siRNAs were used: anti-firefly luciferase (siFLuc): 5'-CUU-ACG-CUG-AGU-ACU-UCG-AdTdT-3' (SEQ ID No 5) (sense strand) and the corresponding scrambled version of the anti-luciferase (siSCR): 5'-CAU-CAU-CCC-UGC-CUC-UAC-UdTdT-3' (SEQ ID No 6) (sense strand) as well as the anti-cyclin dependent kinase 4 (siCDK4) siRNA based on: 5'-CAG-AUC-UCG-GUG-AAC-GAU-GdTdT-3' (SEQ ID No 7) (anti-sense strand) and the scrambled version: 5'-AAC-CAC-UCA-ACU-UUU-UCC-CAA-dTdT-3' (SEQ ID No 8) (anti-sense strand).

The siRNA stock solutions were prepared in RNase-free water, peptide stock solutions as well as CPP:siRNA complexes were prepared as published previously (Konate K, et al. (2016) Optimisation of vectorisation property: a comparative study for a secondary amphipathic peptide. Int J Pharm. 509, 71-84).

Peptide synthesis and modifications: Peptides were purchased from LifeTein or produced in our laboratory (sequences in Table 1) using standard Fmoc chemistry and purified by HPLC/MS (>95% purity). PEG entity was grafted on the purified CPPs, bearing a cysteine residue on its N-terminal end using a 4 molar excess of PEG maleimide 2,000 (Nanocs) during 23 h at room temperature. RGD targeting sequence was grafted during the synthesis on CPPs bearing an amino hexanoic acid as linker at the N-terminal end.

Peptide structure prediction: PEPstrMOD server was used to predict the tertiary structure of WRAPS (http://osddlinux.osdd.net/raghava/pepstrmod/) (H. Kaur, et al., (2007) Protein Pept. Lett. 14, 626-630; S. Singh, et al., (2015) Biol. Direct. 10, 73).

Circular dichroism (CD) measurements. CD spectra were recorded on a Jasco 810 (Japan) dichrograph in quartz suprasil cells (Hellma) with an optical path of 1 mm for peptide in solution or in the presence of liposomes vesicles. The same concentrations of peptide (40 µM) was used for each condition. Spectra were obtained from 3 accumulations between 190 nm and 260 nm with a data pitch of 0.5 nm, a bandwidth of 1 nm and a standard sensitivity.

Agarose gel shift assay. CPPs:siRNA complexes were formed at different ratios in 5% glucose and pre-incubated for 30 min at room temperature. Each sample was analyzed by agarose gel (1% w/v) electrophoresis stained with GelRed (Interchim) for UV detection as descripted previously.

Dynamic light scattering (DLS) and Zeta potential (ZP). CPPs:siRNA nanoparticles were evaluated with a Zetasizer NanoZS (Malvern) in terms of mean size (Z-average) of the particle distribution and of homogeneity (PdI). Zeta potential was determined in 5% glucose+5 mM of NaCl. All results were obtained from three independent measurements (three runs for each measurement at 25° C.).

Transmission Electron Microscopy (TEM). For transmission electron microscopy (TEM), a drop of 5 µl of suspension was deposited on a carbon coated 300 mesh grid for 1 minute, blotted dry by touching filter paper and then placed on a 2% uranyl acetate solution drop. After 1 minute the excess stain was removed by touching the edge with a filter paper, the grid was dried at room temperature for few minutes and examined using a Jeol 1200EX2 Transmission Electron Microscope operating at 100 kV accelerating voltage. Data were collected with a SIS Olympus Quemesa CCD camera.

Culture conditions. U87 MG, human glioblastoma stably transfected with firefly and Nanoluc luciferases (FLuc-NLuc) encoding plasmid (Aldrian G et al., J. Control. Release 2017) were grown in a complete medium: DMEM with GlutaMAX™ (Life Technologies), penicillin/streptomycin (Life Technologies), 10% heat-inactivated fetal bovine serum (FBS, PAA), non-essential amino acids NEAA 1× (LifeTechnologies). Furthermore, hygromycine B (Invitrogen, 50 µg/ml) was added as selection antibiotic.

Keratin forming cell line derived from Hela (KB), murine neuroblastoma cell line (Neuro2a), human hepato carcinoma cell line (HuH7), human breast carcinoma cell line (MCF7) and adenocarcinomic human alveolar basal epithelial cell line (A549) were grown in the same complete medium without the addition of selection antibiotics.

Murine prostate carcinoma cell line (RM1) was grown in the same complete medium with the addition of blasticidin S (Invitrogen, 10 µg/mL) and human colon carcinoma cell line (HT29), rectum carcinoma cell line (CMT93) and murine gliomablastoma cell line (GL261) with the addition of hygromycine B (Invitrogen, 1,400 µg/mL, 500 µg/mL and 150 µg/mL, respectively) as selection antibiotics.

Human breast adenocarcinoma (MDA-MB-231) was grown in the same complete medium with the addition of G418 (Invitrogen, 100 µg/mL) selection antibiotics.

The immortalized human bronchial epithelial cell line BEAS-2B, obtained from ATCC, was grown in Dulbecco's Modified Eagle Medium (DMEM, Fisher Scientific) completed with 5% foetal bovine serum (FBS) (Eurobio), 1% Ultroser G (Pall BioSepra), 1% antibiotic-antimycotic (Life Technologies SAS) and 1% L-glutamine (Life Technologies SAS) T-large immortalized mouse embryonic fibroblasts (MEF) were grown in DMEM/F12 medium (Life Technologies), supplemented with penicillin/streptomycin (Life Technologies) and 10% heat-inactivated fetal bovine serum (FBS, PAA).

All cells were maintained in a humidified incubator with 5% $CO_2$ at 37° C.

Cell culture and transient transfection: 200,000 Beas-2b cells were seeded in 6-well plates as described previously (Viart V et al. Eur Respir J. 2015). Cells were transfected with 1 µg pm-cDNA-CFTR-3'UTR using JetPEI® or CPP2 and with 100 nM MBBO using RNAiMAX or CPP 1.

RNA extraction and RT-qPCR: Total RNA was extracted, reverse transcribed and amplified as previously described (Viart V et al. Eur J Hum Genet 2012). Reverse transcription was performed using 1 µg of total RNA and MMLV reverse transcriptase and qPCR was performed with a 1:10 dilution of first strand DNA. The relative expression levels were calculated using the comparative DDCt method with GAPDH mRNA as endogenous control.

Clonogenic assay. MEF cells were seeded in 6-well plates (250 cells/well). 24 h after seeding, the cells were incubated with the nanoparticles (R=20, 50 nM siRNA) for 14 days. For colony visualization, the cells were fixed with a solution of methanol:acetic acid (3:1) for 20 min, at 4° C. and labelled with a solution of Giemsa (Sigma Aldrich)/$H_2O$ (3.5:10) for 20 min, at room temperature. Remaining staining solution was removed with water and the plates were dried for some hours. Each well was photographed and all colonies were counted.

Transfection experiments. For Luciferase assay, the different cells (5,000 cells per well) were seeded 24 h before experiment into 96-well plates using the corresponding medium as described above. The next day, nanoparticles were formed by mixing siRNA and CPPs (equal volumes, "siRNA on CPPs") in 5% glucose water, followed by an incubation of 30 min at 37° C. In the meantime, the growth medium covering the cells was replaced by 70 µL of fresh pre-warmed serum-free DMEM. 30 µL of the nanoparticle solutions were added directly to the cells and incubated 1.5 h at 37° C. After the addition of DMEM supplemented with 20% FBS (final FBS concentration=10%), cells were further incubated for 36 h and finally lysed for the luciferase detection. For transfection in the presence of serum, cells were incubated with nanoparticles in DMEM+10% FBS for 1.5 h at 37° C., and then DMEM supplemented with 10% FBS were added to the cells which were further incubated for 36 h before the final cell lyses for the luciferase detection.

For Western blot assay, 75,000 U87 cells/mL per well were seeded 24 h before experiment into 24-well plates using the corresponding medium as described above. For standard incubation, the cells were incubated with 175 µL of fresh pre-warmed serum-free DMEM+75 µL of the nanoparticle solutions. After 1.5 h of incubation, 250 µL DMEM+20% FBS were added to each well without withdrawing the transfection reagents, and cells were then incubated for another 24 h. The experimental procedure was designed to test peptide:siRNA nanoparticles at a peptide:siRNA molar ratio of R=20, containing siRNA concentrations of 5, 10 and 20 nM in a final volume of 500 µL. After the addition of DMEM+20% FBS (10% FBS final), cells were further incubated for 24 h and finally lysed for CDK4 western blotting detection.

For microscopy experiments, 300,000 U87 cells were seeded 24 h before imaging into glass bottom dishes (FluoroDish, World Precision Instruments). Before experiments, cells were washed twice with D-PBS and covered with 1,600 µL of complete medium. Afterwards, 400 µL of NPs (peptide:siRNA; R=20, siRNA=20 nM), formulated in an aqueous solution of 5% glucose were directly added on the cells as previously described.

Measurement of cell cytotoxicity. Evaluation of cytotoxicity induced by the nanoparticles was performed using Cytotoxicity Detection Kit$^{Plus}$ (LDH, Roche Diagnostics) on 50 µL of supernatant, by following the manufacturer instructions.

Luciferase reporter gene silencing assay. The evaluation of siRNA delivery using the different vectors was carried out by measuring the remaining luciferase firefly (FLuc) activity in cell lysates. Briefly, after 36 h, the medium covering the cells was carefully removed and replaced by 50 µL of 0.5× Passive Lysis Buffer (PLB; Promega). After 30 min of shaking at 4° C., plates containing the cells were centrifuged (10 min, 1,800 rpm, 4° C.) and 5 µL of each cell lysate supernatant were finally transferred into a white 96-well plate. For the U87-FLuc-NLuc cells, both luciferase activities were quantified using a plate-reading luminometer (POLARstar Omega, BMG Labtech) using half-diluted Dual Luciferase Assay Reagents (Promega) as reported elsewhere (G. Aldrian, et al., (2017) J. Control. Release Off. J. Control. Release Soc. 256, 79-91). The results were expressed as percentage of relative light units (RLU) for each luciferase normalized first to non-treated cells (% FLuc and % NLuc) and then normalized to the value of % NLuc to obtain the Relative Luc Activity (% FLuc/% NLuc).

For the other cell lines having only the FLuc expression, the luciferase activity was quantified using a plate-reading luminometer using half-diluted Luciferase Assay Reagents (Promega). The results were expressed as percentage of relative light units (RLU) normalized to the non-treated cells (% FLuc).

Western blotting. Transfected cells washed in PBS, and lysed in RIPA buffer [50 mM Tris pH 8.0, 150 mM sodium chloride, 1% Triton X-100, 0.1% SDS (sodium dodecyl sulfate, Sigma-Aldrich), including protease inhibitors (SigmaFAST, Sigma-Aldrich)]. Cells were incubated for 5 min on ice with 130 µL/24-well lysis buffer. Thereafter, cells were scrapped and transferred in a 1.5 ml tube. After 5 min on ice, the cell lysates were centrifuged (10 min, 13,400 rpm, 4° C.), supernatants were collected and protein concentrations were determined using the Pierce BCA Protein Assay (ThermoFisher). Cell extracts (0.25-0.38 µg/µL) were separated by 4-20% Mini-PROTEAN® TGX™ Precast Gel (Bio-Rad). After electrophoresis, samples were transferred onto Trans-Blot® Turbo™ Mini PVDF Transfer membrane (Bio-Rad). As antibodies (all from Cell Signaling), we used anti-cyclin B1 mouse mAb V152, anti-CDK4 rabbit mAb D9G3E, anti-Vinculin rabbit mAb E1E9V, anti-mouse IgG HRP and anti-rabbit IgG HRP. Blots were revealed with the Pierce ECL plus Western blotting substrate (ThermoFisher)

on an Amersham imager 600 (GE Healthcare Life Science). The signal intensities of the blots were quantified by Image J.

Confocal microscopy. For cell imaging by confocal microscopy, an inverted LSM780 multiphoton microscope (Zeiss) was used. After the addition of the NPs, cells were incubated for 1 h in a humidified incubator with 5% $CO_2$ at 37° C. 10 min before the end of the incubation, Hoechst 33342 dye was added to the cell for nucleus labeling. Afterwards, cells were washed twice with D-PBS and covered with FluoroBrite DMEM medium (Life Technologies). The confocal images were projected and treated with the ImageJ software.

For Spinning disk experiment, an inverted microscope (Nikon Ti Eclipse) coupled to a spinning disk (ANDOR) system was used to study the internalization kinetics of the NPs inside living cells. After the addition of the NPs, cells were maintained at 37° C. by a cage incubator (Okolab) and images were directly recorded every 5 s for 1,200 s with an EM-CCD camera (iXon Ultra) and projected with the Andor IQ3 software. Control experiments were performed to ensure that no emission bleed through was observed between the different channels. All images were treated with the ImageJ software.

In vivo mice experiments: Immunodeficient NOG (NOD/SCID/IL-2Rγnull) mice between 6 to 10 weeks old were reared at the University of Bordeaux animal facilities. Mice, maintained under specific pathogen-free conditions, were maintained in standard conditions under a 12 h light/dark cycle with water and food provided ad libitum. Anesthesia was performed using 2% isoflurane (Belamont, Nicholas Piramal Limited, London, UK) in air. The regions of the mice to be imaged were previously shaved with clippers and depilatory cream.

Subcutaneous tumors were generated by injection of U87-FRT-CMV-Fluc-CMV-Nluc cells ($2 \times 10^6$ cells/100 μL PBS) on the right posterior leg of the mouse. Subcutaneous tumors were imaged 4 weeks after implantation.

mRNA extraction and quantitative RT-PCR: Total mRNA was isolated from U87 cells using Trizol (Thermo Fisher Scientific). cDNA synthesis was performed using 1 mg of total RNA using NucleoSpin RNA (Macherey-Nagel). Quantitative PCR was performed using Fast SYBR Green Master Mix (Invitrogen) with the use of MyIq Quantitative (Bio-Rad). Primers for Fluc amplification were Fluc-Fw: TCCATTCCATCACGGTTTTGG (SEQ ID No 9), Fluc-Rv: GCTATGTCTCCAGAATGTAGC (SEQ ID No 10), GAPDH-Fw: GCCAAGGTCATCCATGACAAC (SEQ ID No 11), GAPDH-Rv: GAGGAGTGGGTGTCGCTGTTG (SEQ ID No 12).

Reactions were run in triplicate in three independent experiments. Expression data were normalized to the geometric mean of housekeeping gene GAPDH to control the variability in expression levels and were analyzed using the $2^{-DDCt}$ method.

Results

1. Characterization of the Peptides:

In the present experimentations, several amphipathic peptides have been studied and compared for their ability to form peptide-based nanoparticles (PBN) to deliver therapeutic molecules (Table 1). Peptides CPP1 to CPP4 belongs to peptides of the invention and are composed of 3 kinds of amino acids: leucine, arginine and tryptophan residues. The peptides are 15 to 16 amino acids long with a C-terminal portion having an amide group ($—CONH_2$) and an amine ($—NH_2$) at the N-terminal portion. All peptides of the patent application alone have a net positive charge of +5 (or of +4 if an entity is coupled to the N-terminal part).

TABLE 1

Sequences of cell penetrating peptides

| ID | Sequences | CPP AA | Charges | Nb W |
|---|---|---|---|---|
| CPP1 | LLWRLWRLLWRLWRLL (SEQ ID No 1) | 16 | 5 | 4 |
| CPP1-1 | LWRLWRLLWRLWRL (SEQ ID No 13) | 14 | 5 | 4 |
| CPP2 | LLRLLRWWWRLLRLL (SEQ ID No 2) | 15 | 5 | 3 |
| CPP2-1 | LRLRWWWRLRL (SEQ ID No 14) | 11 | 5 | 3 |
| CPP2-2 | LLRLRWWWRLRLL (SEQ ID No 15) | 13 | 5 | 3 |
| CPP2-3 | LRLLRWWWRLLRL (SEQ ID No 16) | 13 | 5 | 3 |
| CPP3 | LLRLLRWWRLLRLL (SEQ ID No 3) | 14 | 5 | 2 |
| CPP4 | LLRLLRWWWWRLLRLL (SEQ ID No 4) | 16 | 5 | 4 |
| C6M1 | RLWRLLWRLWRRLWRLLR (SEQ ID No 17) | 18 | 8 | 4 |
| C6M1-L | RLWRLWRLWRRLWRLLR (SEQ ID No 18) | 17 | 8 | 4 |
| P-CPP1 | $PEG_{2000}$-LLWRLWRLLWRLWRLL | 16 | 4 | 4 |
| P-CPP2 | $PEG_{2000}$-LLRLLRWWWRLLRLL | 15 | 4 | 3 |
| R-CPP2 | RGD-Ahx-LLRLLRWWWRLLRLL | 15 | 4 | 3 |
| CPP1-4R | RLLWRLW-----LWRLLR (SEQ ID No 19) | 13 | 5 | 3 |
| CPP1-6R | RLLWRLWRLLWRLWRLLR (SEQ ID No 20) | 18 | 7 | 4 |
| CPP2-4R | RLLRLL-WWW-LLRLLR (SEQ ID No 21) | 15 | 5 | 3 |
| CPP2-6R | RLLRLLRWWWRLLRLLR (SEQ ID No 22) | 17 | 7 | 3 |

Footnote:
CPP AA = number of amino acids of the CPP sequence.

Figure 1:
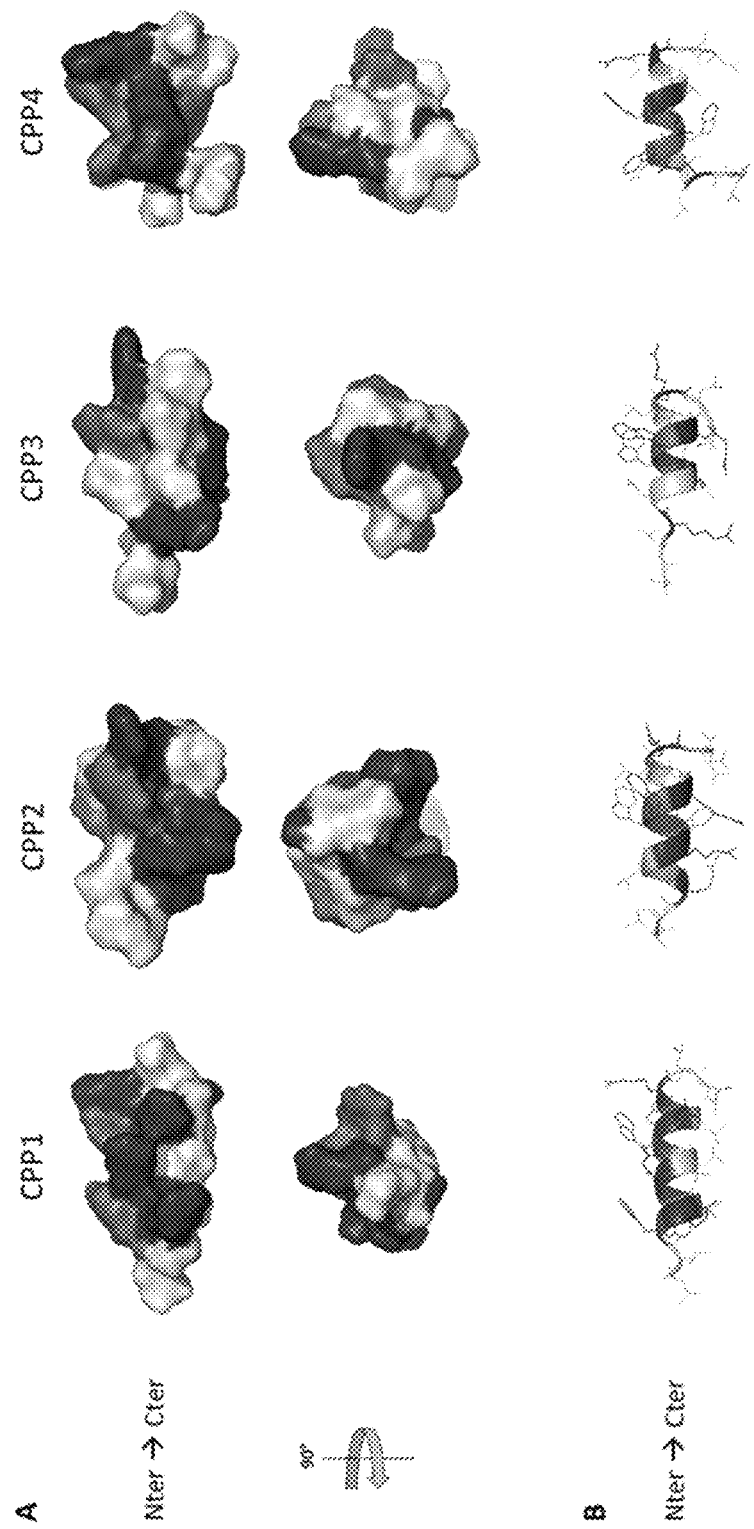
FIG. 1: Prediction of the 3D structures of the used amphipathic peptides by PEPstrMOD under hydrophilic condition. Surface and ribbon representation of the peptides.

To check structural properties of CPPs, first an in silico prediction of the 3D structure of each peptide was undergone. Sequences of CPP1 to CPP4 were submitted to PepStrMOD server in a hydrophilic environment. After computation, the peptide models generated by PepstrMOD revealed that all peptides adopted α-helical structure (FIG. 1). CPP1 and CPP2 seemed to present a more pronounced helicity than the other models.

The predicted structures were then compared to experimental investigations. Circular dichroism spectra were recorded for the peptides free in solution, afterwards for the peptides in the presence of siRNA and then after the addition of liposomes. All peptides (CPP1, CPP2, CPP3 and CPP4) adopt an alpha helical structure in the presence of siRNA molecules, and even in the presence of neutral or negatively charged lipids ("large unilamellar vesicles" (LUVs)) as described in Table 2.

TABLE 2

Conformational analyses of amphipathic peptides by circular dichroism.

| | PEPTIDE | | |
| --- | --- | --- | --- |
| | | +siRNA | |
| ID | | +neutral LUVs | +charged LUVs |
| CPP1 | rc/helix  helix | helix | helix |
| CPP2 | turn/rc  helix | helix | helix |
| CPP3 | turn  helix | helix | helix |
| CPP4 | turn  helix | helix | helix |

Footnotes:
Random coiled (rc) conformation has a positive band at 212 nm and a negative one around 195 nm.
Helical conformation is characterized by two minima at 207 nm and 222 nm and one maximum around 191 nm.
Turn-like structure is observed with two minima at 200 nm and 228 nm.
CPP:siRNA molar ratio of R 20 and CPP:lipid of r 10 with a CPP concentration of 40 μM.

2. Colloidal Characterization of the Amphipathic Peptides

The conformational changes detected by CD suggested that nearly all CPPs interact with siRNA. To assess complexation of siRNA, the formation of CPP:siRNA complexes was investigated by agarose shift assay (FIG. 2). siRNA alone was able to migrate into the agarose gel (=100% signal) but when complexed with CPPs, the peptides prevented oligonucleotide migration in a molar ratio-dependent manner. CPP1, CPP2, CPP3 and CPP4 were clearly able to complex siRNA in a similar manner with optimal complexation at peptide:siRNA molar ratios of R=20 and R=40.

Colloidal features of CPP:siRNA complexes (5% glucose, R=20) were characterized in terms of nanoparticle size and homogeneity by dynamic light scattering (DLS). Intensity measurements (%) revealed that CPP1, CPP2, CPP3 and CPP4 formed PBN with diameter between 80 nm to 200 nm with polydispersity indexes (PdI) around 0.3 (Table 3). The nanoparticle size distribution based on number (%) suggested the presence of smaller nanoparticles in addition to those found by the intensity-based size distribution. These smaller particles had diameters between 20 nm to 50 nm for the four CPP:siRNA (Table 3). More importantly, both measured size values did not change significantly even after 72 h storage at 4° C. (data not shown).

The PBNs composed of CPP1:siRNA or CPP2:siRNA have both a positive charge surface (zeta potential measurements, Table 3) and a globular shape as measured by transmission electron microscopy (FIG. 2B).

TABLE 3

CPP characterization by DLS measurements.

| | Mean size (nm) | | | |
| --- | --- | --- | --- | --- |
| | I (%) | Nb (%) | PdI | ZP (mV) |
| CPP1 | 73.3 ± 7.4 | 26.5 ± 4.1 | 0.38 ± 0.08 | 42.2 ± 4.5 |
| CPP1-4R | 1012 ± 984 | 422 ± 498 | 0.50 ± 0.04 | n.d. |
| CPP1-6R | 125.3 ± 65.1 | 23.3 ± 3.4 | 0.42 ± 0.08 | n.d. |
| CPP2* | 80.0 ± 4.9 | 35.7 ± 7.3 | 0.29 ± 0.05 | 28.8 ± 0.9 |
| CPP2-4R | 65.0 ± 1.8 | 26.0 ± 4.3 | 0.37 ± 0.03 | n.d. |
| CPP2-6R | 59.8 ± 9.3 | 25.9 ± 3.9 | 0.34 ± 0.03 | n.d. |
| CPP4 | 122.0 ± 71.5 | 23.6 ± 7.9 | 0.44 ± 0.11 | n.d. |

Footnotes:
All CPP:siRNA complexes were formed at R = 20 with a siRNA concentration of 500 nM in an aqueous solution of 5% glucose for mean size acquisition and in an aqueous solution of 5% glucose with 5 mM NaCl for ZP evaluation.
n ≥ 2 independent formulations (with 3 measures per run).
n.d.: not determine.
*ZP measured in 5% glucose with 1 mM NaCl.

3. Efficacy of the siRNA-Loaded CPP Nanoparticles Depending on the Formulation

The efficacy of the siRNA-loaded CPP nanoparticles have been evaluated depending on the applied concentration during the formulation.

Two different formulations have been compared:
1) The dilution condition: The complexes were formulated at higher concentration (e.g. CPP[10 μM]:siRNA[0.5 μM]) followed by dilution to a final siRNA concentrations of 5 nM, 10 nM and 20 nM for the cell culture assay.
2) The volume:volume condition: The CPP and the siRNA solutions were prepared separately and then mixed together to obtain the final siRNA concentrations of 5 nM, 10 nM and 20 nM for the cell culture assay.

As exemplified by the formulation done with CPP2, it was that the knock-down efficiency of the nanoparticles could be increased, depending on the applied formulation procedure (FIG. 14). The dilution condition seems to induce a higher knock-down efficiency (2-fold increase). This is of particular interest for the transfection of cells known to be "difficult" to transfect.

4. Amphipathic Peptides could be Used to Formulate Plasmids:

The CPP1 and CPP2 peptides formed complexes when they were associated with oligonucleotides such as a plasmid (FIG. 3). The formation of the complexes was visualized using an agarose gel (0.5%) as described above for the complexation of the CPP with a siRNA. At a charge ratio (CR) corresponding to the charge neutrality (CR=1) between the CPP (positive charge) and the plasmid (negative charge), the plasmid was complexed by the CPP. The bulky CPP:plasmid complex was then no longer able to migrate into the agarose gel.

The intensity of the plasmid band alone was normalized to 100%. By successively increasing the CPP:plasmid charge ratio, the complexation of the pGL3 plasmid (6.56 kbp) was obtained, proportionally reducing its migration in the agarose gel (0.5%).

In order to analyze the transfection potential of plasmid-loaded CPP nanoparticles, MCF7 (human breast carcinoma) and MEF (mouse embryonic fibroblast) cells were transfected with a plasmid encoding the firefly luciferase (pGL3). After 24 h incubation with CPP2:pGL3 (CR=1), cells were lyzed and the expression of the firefly luciferase was quantified by adding its substrate (kit from Promega). As shown in FIGS. 3 B and 3 C, a dose-dependent increase in firefly luciferase activity was observed, which correlates to an increased protein expression, compared to non-treated cells.

In conclusion, the PBNs could be also used to transfect plasmids, as shown previously with siRNA.

5. Characterization of the Cellular Activity of CPP:siRNA Nanoparticles in a Luciferase Screening Assay Cellular activity of CPP-based nanoparticles was evaluated in a luciferase screening assay, as previously described (L. N. Patel, et al., (2007) Pharm. Res. 24, 1977-1992; A. Elmquist, et al., (2001) Exp. Cell Res. 269, 237-244)). The knock-down efficiency of the different CPP:siRNA nanoparticles was performed on U87 cell line stably transfected for constitutive expression of FLuc/NLuc reporter genes (U87-FRT-CMV/Fluc-CMV/iRFP-IRES-NLuc).

First of all, we investigated the optimal molar ratio between the peptide and the siRNA (constant concentration of 20 nM) which was required for an effective luciferase knock-down (FIG. 4A). For CPP1, CPP2, CPP3 and CPP4, we observed a significant luciferase knock-down of more than 70% at R=20 which was slightly increased at R=40. In parallel no relative cytotoxicity was observed for all nanoparticle treatments (LDH measurement).

A very promising knock-down results of firefly luciferase were observable after 36 h of total transfection but also after 24 h, representing a significant gain for the experimenter. At molar ratios R 20 and R 40 for CPP2:siRNA as well as for CPP4:siRNA, the relative reduction of the luciferase signal was identical for all conditions (~60-80%) independently of the applied transfection time (FIG. 4B).

Thereafter, the optimal siRNA concentration was elucidated by using the optimal peptide:siRNA molar ratio of R=20 (FIG. 4C). The three PBNs (CPP1, CPP2 and CPP4) displayed a very nice dose-dependent relationship showing a significant knock-down efficiency with an IC50 value of around 7.5 nM. Here again no cytotoxicity was detected for all used conditions.

Finally, we can recognize that the presented nanoparticles induced an equivalent luciferase knock-down reduction as the Lipofectamine® RNAiMAX (a product currently marketed ThermoFisher for siRNA transfection) at the same used siRNA concentration. However, under these conditions we observed a significant cytotoxicity corresponding to 21% with the Lipofectamine® RNAiMAX vectorization (FIG. 4C).

For repeated or long-term application of the nanoparticles, it is preferable to use CPPs in isoform D in order to reduce their degradation by the extra- or intracellular proteases. In this context, the efficiency of the CPP2:siRNA nanoparticles was evaluated using the peptide in the L or D configuration.

The study of the colloidal properties revealed that the peptide CPP2 in isoform D (CPP2 [D]) forms nanoparticles of identical size to the CPP2 [L], as confirmed by DLS (I %=70±11 nm, Nb %=31±1 nm, PdI=0.302±0.024, see also Table 3 for CPP2 [L]).

In parallel, the reduction of the firefly luciferase expression was observed in a dose-dependent manner (1 nM to 20 nM siRNA) at a constant ratio of R 20 and thus independently of the isomerization of the peptide (CPP2 [D] and CPP2 [L]) (FIG. 5).

To simulate an in vivo application, the nanoparticles were incubated in the presence of serum to mimic potential interactions with serum proteins when administered by an intravenous injection. The presence of serum (10%) had no significant deleterious influence on the activity of the nanoparticles in terms of firefly luciferase silencing at 15 nM and 20 nM of siRNA for CPP1 and from 10 nM to 20 nM siRNA for CPP2 (FIG. 6). A reduction in the luciferase activity of around 70% was observed in the presence of 10% serum which corresponded to the condition without serum.

Finally, we have demonstrated that siRNA transfection by the CPPs was reproducible from one laboratory to another and independently of the detection method used. In this comparison, U87 cells were incubated with CPP2:siRNA nanoparticles at three concentrations of siRNA (5 nM, 10 nM and 20 nM). After incubation, the cells were lysed and the activities of firefly luciferases and NanoLuc quantified in the cell lysate transferred into a 96-well plate (Dual Luciferase kit, Promega with PolarStar measurement, BMG) or in tubes (Luciferase Assay Reagent and Nano-Glo Luciferase Assay, Promega with Lumat LB 9507 measurement, Berthold Technologies). In both cases, the values showing the dose-dependent reduction of firefly luciferase expression were identical (FIG. 7).

6. Comparison of the CPP:siRNA Activity with Other CPPs with Similar Sequences.

Different sequences analogues to the two peptides CPP1 and CPP2 were synthesized to show the importance of amino acid positions (CPP1 versus C6M1) as well as the role of leucine residues (CPP2 versus CPP2-1 to CPP2-3, Table 1).

In order to show that our CPPs have a better efficiency in terms of siRNA transfection than the C6M1 peptide published by Jafari et al. (2013), a direct comparison has been made. The C6M1-L sequence was included representing a C6M1 analogue with a leucine deletion in the leucine doublet in the N-terminal position of the peptide sequence (Table 1 and FIG. 8A).

Human glioblastoma cells (U87) overexpressing firefly luciferase were incubated with siRNA-encapsulating nanoparticles (siFluc or siSCR as a negative control) formulated with the four vector peptides CPP1, C6M1, C6M1-L and CPP2. These formulations were performed in parallel in the same way for all peptides using the same concentrations (CPP=200 nM and siRNA=10 nM). All solutions were subsequently incubated for 1.5 h in a P96 plate containing 5.000 cells/well in order to avoid biases between the incubations.

After luciferase activity measurement, we clearly showed that CPP1:siRNA and CPP2:siRNA could induce a 90% reduction in luciferase expression. In comparison, we observed a luciferase knock-down which corresponds to only 60% for C6M1:siRNA and to 40% C6M1-L:siRNA (FIG. 8A).

In conclusion, the CPP1 peptide was 3-fold more active than C6M1 and 6-fold more active than C6M1-L in terms of reduced luciferase expression (p=**** for both comparison, One-way ANOVA with a Tukey post-test). Additionally, we could show that even the CPP2 peptide was more effective than C6M1 (2-fold) and C6M1-L (3.5-fold).

In order to understand the importance of leucine "doublets" in peptide sequences, we generated analogues by removing leucine residues at different positions (see Table 1). When replacing the "doublets" of the middle only (CPP2-1) or all "doublets" (CPP2-2) of the CPP2 sequence by simple leucine residues, we observed the total inactivity of the nanoparticles in the luciferase assay (FIG. 8B).

In a second step, we wanted to analyze the importance of the "doublets" in the N- and C-terminal positions of the CPP1 and CPP2 sequence (CPP1-1 and CPP2-3, respectively). This deletion had also an impact on the activity of nanoparticles (siRNA-FLuc) in cellulo (FIG. 8B):

The nanoparticles CPP2-3:siFLuc showed no activity in terms of luciferase silencing compared to that observed with CPP2:siFluc PBN.

The nanoparticles CPP1-1:siFLuc had a reduced inhibition activity, especially at the siRNA concentrations of 10 nM and 20 nM which corresponds to a 3× and 5× times lower activity of the PBN compared to the CPP1:siFLuc nanoparticle at the same concentrations.

In a third step, we wanted to confirm the consensus sequence of our developed CPPs and their respective behavior of them compared to C6M1 and C6M1-L. Therefore, peptide sequences bearing additional arginine residues at the peptide sequence termini (N-terminus and C-terminus) were synthesized (see sequence CPP1-6R and CPP2-6R in Table 1).

However, the addition of two arginine within the sequence will also increase the total net charge of the peptide. To obtain the same net charge than the parental peptide, two further peptides bearing N- and C-terminal arginine residues but also deleted of two internal arginine residues were designed (CPP1-4R and CPP2-4R, Table 1). In all situations, the arginine addition at both ends of the peptides reduced the activity of nanoparticles (siRNA-FLuc) in cellulo (FIG. 8B):

The nanoparticles CPP1-4R:siFLuc showed no activity in terms of luciferase silencing compared to that observed with CPP1:siFluc PBN. The nanoparticles CPP1-6R:siFLuc had a reduced inhibition activity which corresponds to a 4× (5 nM siRNA) and 3× times (10 nM and 20 nM siRNA) lower activity of the PBN compared to the CPP1:siFLuc nanoparticle at the same concentrations.

The nanoparticles CPP2-4R:siFLuc and CPP2-6R had a reduced inhibition activity which corresponds to a 3× to 4× times lower activity of the PBN compared to the CPP2:siFLuc nanoparticle at all siRNA concentrations. Additionally, CPP2-4R showed some variability in the the luciferase activity measurement which is probably due to some cytotoxic effect of the nanoparticle incubation.

DLS measurements explained the obtained results (Table 3): CPP1-4R:siRNA were more aggregated than parent nanoparticles, CPP1-6R:siRNA particles were bigger and more poly-dispersed than CPP1:siRNA, CPP2-4R:siRNA and CPP2-6R:siRNA seemed to form smaller nanoparticles but appeared more poly-dispersed than those obtained with CPP2:siRNA.

In conclusion, CPP1 and CPP2 have both the best amino acid combination allowing the stable formation of nanoparticles with the highest knock-down efficiency.

7. Examples of the Transfection Efficiency of the CPP:siRNA Nanoparticles:

Since they showed the best transfection efficiencies, CPP1 and CPP2 were selected for additional cellular investigations and developments. Both peptides were tested on different cell lines in order to estimate their potential as universal transfection agents. A FLuc gene silencing of 50% to 80% was detected using 20 nM siRNA in U87 (human gliomablastoma), KB (keratin forming cell derived from Hela), HuH7 (human hepato carcinoma) and Neuro2a (murine neuroblastoma), MCF7 (human breast carcinoma), MDA-MB-231 (human breast adenocarcinoma) cells, using 50 nM siRNA in CMT93 (rectum carcinoma), MEF-RAS: Ras-modified mouse embryonic fibroblasts, A549: adenocarcinomic human alveolar basal epithelial cells, HT29 (human colon carcinoma) and RM1 (murine prostate carcinoma) cells and with 100 nM siRNA in GL261 (murine gliomablastoma) cells, suggesting that some cell lines required higher siRNA doses to reach a comparable knock-down efficiency (FIG. 9A).

CPP1- and CPP2-based NPs were also applied to target the endogenous protein cyclin-dependent kinase 4 (CDK4), known to be overexpressed in glioblastoma (D. W. Parsons et al., (2008) An integrated genomic analysis of human glioblastoma multiforme, Science. 321, 1807-1812). A significant CDK4 knock-down was observed for both peptide with an inhibition of CDK4 expression corresponding to 30%, 60% and 80% for 5 nM, 10 nM and 20 nM, respectively. CPP1:siCDK4 seemed to have a slightly higher effect than CPP2:siCDK4 on CDK knock-down (FIG. 9B).

A direct comparison with Lipofectamine® RNAiMAX (lipid transfection molecule marketed by ThermoFisher) clearly showed the advantages of the PBN transfection system (FIG. 9C). Both transfection systems were effective with a significant CDK4 knock-down but the Lipofectamine® RNAiMAX condition showed remarkable cytotoxic effects already at low concentration. The cytotoxicity could be observed in Western blot using the internal control (Vinculin expression: bars in dark gray) or the total protein concentrations (measured by the BCA kit, value in red).

At siCDK4 concentration of 50 nM, CPP1 induced a CDK4 knock-down of more than 80% without any cytotoxicity. On the other hand, when siRNA was transfected with the Lipofectamine® RNAiMAX agent, the knock-down was identical but associated with a significant reduction in the amount of the total cellular proteins and of the vinculin, indicating a significant cytotoxicity of the transfection agent (red dashed line).

Cytotoxicity of CPP2 was also observed through clonogenic assay (FIG. 9D) compared to both RNAiMAX conditions which exhibited extremely toxic profile for cell survival and proliferation. All other CPP2 conditions had no effect on cell survival and proliferation compared to untreated cells. As expected, the control condition using siRNA directed against the Cyclin D1 protein implemented in cell cycle showed a 50% reduction in cell survival.

The effect of CPP2-based NPs on the endogenous protein CDK4 was also evaluated after three successive administrations of NPs during three subsequent days of culture (FIG. 9E). A significant CDK4 knock-down was detected for all conditions but a cumulative effect was clearly observed for three successive doses of 20 nM siRNA (dose3) compared to a single administration (dose 1), suggesting the potential cumulative impact of CPP2-based NPs over time.

8. Examples of the Transfection Efficiency of the CPP:siRNA Nanoparticles on Cell Suspension:

In order to evaluate the transfection potential of the siRNA-loaded CPP nanoparticles on non-adherent cells (suspension), a so-called inverted transfection on U87 cells was performed. In the "standard" transfection conditions, the cells were plated in a microtiter plate at the desired concentration and after adhesion on the well bottom (6 h to 24 h), the cells were transfected with the nanoparticles. During the "inverted" transfection, the nanoparticles were transferred to a microtiter plate and then the trypsinized cells re-suspended in medium with or without serum were added to the nanoparticles (See FIGS. 15 A and B).

In both cases, CPP1:siFLuc and CPP2:siFLuc showed a dose-dependent silencing of the luciferase gene, which were specific because the CPP:siSCR nanoparticles did not shown any knock-down efficiency. This silencing specificity was observed in medium without or with serum in the same manner. However, the silencing efficiency of the inverted transfection needed a slightly higher dose of siRNA (50 nM instead of 20 nM) to obtain the same 80-90% knock-down of the "standard" transfection.

Next, the transfection potential of the CPP2:siFLuc on non-adherent cells such as the firefly luciferase stably transfected U937 human macrophage was evaluated (FIG. 15C). CPP2:siFLuc nanoparticles showed a dose-dependent silencing of the luciferase gene, which were specific of the transfection because siFLuc alone did not shown any knock-down efficiency. The silencing efficiency was determined with 40%, 80% and 100% for the siRNA concentrations of 10 nM, 20 nM and 50 nM, respectively.

9. Co-Transfection of CPP1:MBBO and CPP2:Plasmid in the Context of Cystic Fibrosis Cystic fibrosis (CF) is a genetic disorder that affects mostly the lungs, but also the pancreas, liver, kidneys, and intestine. It is caused by the presence of mutations in both copies of the gene for the cystic fibrosis transmembrane conductance regulator (CFTR) protein. Recently, it has been found that CFTR was post-transcriptionally regulated by micorRNAs, such as miR-145 and miR-494 (Gillen A E et al. Biochem J. 2011; Megiorni F et al. Plos One, 2011; Ramachandran S et al. PNAS, 2012, Viart V et al. Eur Respir J. 2015). Several miRNAs including miR-145 are expressed in primary human airway epithelial cells, where CFTR expression is repressed (Gillen A E et al. Biochem J, 2011) or are deregulated in CF patients (Oglesby I K et al. J immunol, 2013; Ramachandran S et al. AJRCMB. 2013).

The group of Dr. M. Taulan-Cardars has designed target-site blocker (TSB, also named miRNA binding-blocker oligonculeotides, MBBO) to prevent binding of several miRNAs including miR-101, miR-600, miR-145 and miR-384 to the 3'-UTR of the CFTR gene. (PCT/EP2014/069522). This MBBO could be encapsulated by CPP1 in a molar ratio dependent manner with a full complexation at R=5 (FIG. 16 A). Using this molar ratio, we obtained nanoparticles with a mean size of 180 nm as determined by dynamic light scattering (DLS) (FIG. 16 B).

Afterwards, we evaluated the impact of MMBO transfection on the amount of CFTR transcripts in bronchial Beas-2b cells (FIG. 16 C) in comparison with different transfection agents. In a co-transfection experiment, a plasmid encoding the CFTR (pm-cDNA-CFTR-3'UTR, 11.8 kbp) was transfected with different MBBOs (19-28 pb). The CFTR transcript level was first normalized to the house-keeping gene GAPDH (glyceraldehyde-3-phosphate dehydrogenase) and then normalized to the control MBBO (MBP-Ctrl with no 3'-UTR binding property). Three different combinations of transfection agents were analyzed:

Lipofectamin™ RNAiMAX for both CFTR plasmid and MBBO transfection

JetPEI® for CFTR plasmid transfection and CPP1 for MBBO transfection

CPP2 for CFTR plasmid transfection and CPP1 for MBBO transfection.

As shown in FIG. 16 C, the amount of CFTR transcript after CPP2:plasmid/CPP1:MBBO transfection in bronchial Beas-2b cells is 2- to 3-fold higher compared to a transfection using JetPEI®:plasmid/CPP1:MBBO and even 10- to 12-fold higher than the JetPEI®:plasmid/RNAiMAX: MBBO condition. This increase of CFTR transcript is correlated with a better transfection property of the plasmid and the MBBO based on CPP1 and CPP2 peptides-based transfection.

10. Evaluation of the Internalization Kinetics of the siRNA-Loaded PBNs:

CPP1 and CPP2-based nanoparticles displayed a significant efficiency in gene silencing, suggesting an optimal siRNA delivery. We therefore attempted to evaluate their time-dependent cellular internalization. siRNA-loaded PBNs (20 nM siFLuc) were applied on human U87 cells during different incubation times, ranking from 5 min to 90 min, and then the PBN solutions were replaced by medium containing 10% FBS for 36 h. Results revealed that after a 5 min incubation, CPP1 and CPP2 nanoparticles were already able to induce a 40% reduction of FLuc activity, suggesting a fast and significant knock-down of the protein (FIG. 10A). Moreover, a maximum and saturating FLuc silencing was observed after 60 min incubation for both peptide without any cytotoxicity. Compared to FIG. 4C, the maximal knock-down efficiency at 60 min was slightly lower probably because: i) 30 min additional incubation time was missing and ii) the PBN solutions were replaced and not filled with supplemented medium.

Similar time-depending experiments performed with PBNs loaded with siCDK4 revealed after Western blot evaluation a similar result, confirming the fast efficiency of the transfection (FIG. 10B). Here again, first knock-down efficiency could be observed after 5 min incubation reaching a maximal silencing efficiency at 60 min.

To obtain more information about the internalization of the CPP-based nanoparticles, we performed confocal microscopy experiments. Representative images of the siRNA cellular distribution revealed a punctuated pattern (FIG. 10C) comparable to those observed for other PBNs after 1 h incubation (A. Vaissiére, et al., (2017) A retro-inverso cell-penetrating peptide for siRNA delivery, J. Nanobiotechnology. 15, 34; G. Aldrian, et al., (2017) PEGylation rate influences peptide-based nanoparticles mediated siRNA delivery in vitro and in vivo, J. Control. Release Off. J. Control. Release Soc. 256, 79-91; A. Rydstrom, et al., (2011) Direct translocation as major cellular uptake for CADY self-assembling peptide-based nanoparticles, PloS One. 6, e25924). Afterwards, we performed Spinning Disk experiment (FIG. 10D) to evaluate the internalization kinetic of both CPP-based nanoparticles based on the cellular accumulation of the Cy3b-labelled siRNA. As shown in the graphical representation, we observed that the siRNA delivered by both PBNs reached the maximal fluorescence (90%±5%) after ~15 min incubation (900 s to 945 s). The IC50 values of internalization (50%) were obtained after 240 s and 185 s incubation for CPP1 and CPP2 nanoparticles, respectively. This internalization was very fast compared to previously analyzed PBNs, such as RICK:siRNA or 20% PEG-RICK:siRNA reaching the internalization maximum after 120 min incubation (A. Vaissiére, et al., (2017) A retro-inverso cell-penetrating peptide for siRNA delivery, J. Nanobiotechnology. 15, 34; G. Aldrian, et al., (2017) PEGylation rate influences peptide-based nanoparticles mediated siRNA delivery in vitro and in vivo, J. Control. Release Off. J. Control. Release Soc. 256, 79-91). Altogether, the observed fast siRNA internalization kinetic for both CPP-based nanoparticles could be an explanation for the observed knock-down efficacy even after 5 min incubation (FIGS. 10A and 10B).

11. In Vivo Evaluation of the Nanoparticles (Murine Xenograft Model):

In order to evaluate the efficiency of the nanoparticles in vivo, they were injected into subcutaneous tumors (mouse U87-CMV-FLuc-CMV-iRFP-IRES-NLuc cells). For the generation of tumors, U87 cells ($2 \cdot 10^6$ cells/100 µL) were injected subcutaneously on the right leg of B6 albino mice. After tumor growth, the CPP2:siFluc nanoparticles (20 µL) were injected into the middle of the tumor. Bioluminescent imaging (BLI) was performed at Vivoptic (UMS 3767—Bordeaux University) using Lumina LT software (Perkin Elmer Inc.). The mice received an intraperitoneal injection of D-luciferin and the images were taken at 8 min post-injection after the administration of an anaesthetic solution (2% isoflurane).

Representative images of "dual" bioluminescence (Fluc and Nluc) and fluorescence (iRFP) show a reduction in firefly luciferase visible at 24 h (FIG. 11A). This phenomenon was more marked on the average of a larger number of animals (n=11), revealing a reduction of the luciferase signal of 70% (*$p<0.05$) at 24 h (CPP2:siFluc with 15 µg siFluc, R=20) (FIG. 11B). More importantly, the mRNA-Fluc rate dropped by 80% at 48 h post-injection of CPP2:siFluc nanoparticle injection (***$p=0.0009$) (FIG. 11C).

12. Vectorization of a siRNA "Cocktail" by the CPP Nanoparticles:

The CPP-based peptide nanoparticles may also allow the transfer of a "cocktail" of several different siRNAs targeting distinct proteins, as exemplified below for a cocktail of two siRNAs (at the same proportions) (FIG. 12A) as well as for cocktails of two siRNAs (of different proportions) targeting CyclinB1 and CDK4 proteins (FIG. 12B):

13. Evaluation of Highly Modular Nanoparticles (Grafted PBN):

The targeting of nanoparticles has become an essential prerequisite to reduce the internalization of therapeutic molecules in healthy tissues and prevent undesired side-effects. Since some years, targeting molecules such as peptides or sugars have been grafted onto nanoparticles that recognized overexpressed receptors in certain tissues or cell types (F. Danhier et al., (2012) Mol Pharm. 9(11):2961-73; 22; D. M. Copolovici et al., (2014) ACS Nano. 8(3):1972-94; D. Arosio et al., (2017) Recent Pat Anticancer Drug Discov. 12(2):148-168).

In the context of cancer, the targeting sequence composed of three amino acids (RGD) is the most studied one to increase the specificity of a single therapeutic molecule or a vector (U. K. Marelli U K, et al., (2013) Front Oncol. 3:222). This peptide is known to interact specifically with αvβ3 integrin receptors overexpressed on the surface of cancer cells.

In order to carry out a proof of concept for the modulation of the nanoparticles, the linear sequence of RGD (with an aminohexanoic acid linker, Ahx) was grafted on the N-terminal part of the peptide CPP2.

The extension of the CPP2 peptide of 4 residues did not seem to affect the formation of the nanoparticles, as observed using the luciferase assay (FIG. 13A). There is a reduction in the expression of luciferase ~70% comparable to that of naked PBN (FIG. 4). This level of luciferase silencing remained constant, regardless of the percentage of grafted peptide used (ratio between CPP2 alone and RGD-Ahx-CPP2) (FIG. 13B).

The major limitation on the use of peptide-based nanoparticles is their short life in the bloodstream. However, thanks to a plethora peptide chemistry, PBNs can be modified by functional entities to improve their pharmacological properties (T. Lehto, et al., (2016) Drug Deliv. Rev. 106(Pt A), 172-182). In this line, PEGylation is widely used to improve their stability in vivo, to prevent their recognition by the mononuclear phagocytic system (MPS) in the liver and spleen and interactions with blood components. For example, Genexol-PM [methoxy-PEG-poly (D, L-lactide) Taxol] is the first polymer-based micellar nanoparticle showing real success in Phase II clinical trials in the United States.

In this context, a proof of concept has been realized and showed that the peptide nanoparticles described in this patent can be grafted by PEG entities and even multi-grafted (FIG. 13C). The addition of 20% PEG-CPP had no significant effect on the activity of the nanoparticles. Only the condition of 100% PEG-CPP completely inhibited it. These results correlated with data obtained with PEG-RICK (G. Aldrian, et al., (2017) J. Control. Release Off. J. Control. Release Soc. 256, 79-91).

Furthermore, when the addition of PEG-CPP did not exceed 20%, the formulation of a tripartite mixture, via the insertion of the targeting RGD peptide sequence (CPP2:20% RGD-Ahx-CPP2:20% PEG-CPP2), showed the same potential for reducing luciferase activity as naked nanoparticles (CPP2) (FIG. 13D).

The invention claimed is:

1. A non-naturally occurring cell penetrating peptide that is 14 to 16 amino acid residues in length and has an amino acid sequence of LL-[X]n-LL, wherein X is selected from R, L and W, and n=10 to 12, and wherein [X]n contains 4 R, 4 L and between 2 and 4 W amino acid residues.

2. The peptide according to claim 1, said peptide having the amino acid sequence LL-[X]m-RLL, wherein m=9 to 11.

3. The peptide according to claim 1, wherein [X]n has either clustered or scattered W residues.

4. The peptide according to claim 1, wherein [X]n has at least one cluster consisting of LL.

5. The peptide according to claim 2, wherein [X]m has either clustered or scattered W residues.

6. The peptide according to claim 2, wherein [X]m has at least one cluster consisting of LL.

7. The peptide according to claim 1, wherein the peptide has the amino acid sequence selected from LLWRLWRLL-WRLWRLL (SEQ ID NO:1), LLRLLRWWWRLLRLL (SEQ ID NO:2), LLRLLRWWRLLRLL (SEQ ID NO:3), and LLRLLRWWWWRLLRLL (SEQ ID NO:4).

8. The peptide according to claim 1, wherein the peptide contains L-amino acids and/or D-amino acids.

9. The peptide according to claim 1, wherein the peptide has a net-positive charge of 5.

10. The peptide according to claim 1, wherein the peptide further comprises covalently linked to the C-terminal end of said amino acid sequence, one or more entities selected from a L-amino acid, a D-amino acid, a non-natural amino acid, a cysteamide, a thiol, an amide, a carboxyl, a linear $C_1$-$C_6$ alkyl that is optionally substituted, a ramified $C_1$-$C_6$ alkyl that is optionally substituted, a primary amine, a secondary amine, an osidic derivative, a lipid, a phospholipid, a fatty acid, a cholesterol, a poly-ethylene glycol, a nuclear localization signal, and/or a targeting molecule; and/or wherein the peptide further comprises covalently linked to the N-terminal end of said amino acid sequence, one or more chemical entities selected from a L-amino acid, a D-amino acid, a non-natural amino acid, an amine, an acetyl, a linear $C_1$-$C_6$ alkyl that is optionally substituted, a ramified $C_1$-$C_6$ alkyl that is optionally substituted, a primary amine, a secondary amine, an osidic derivative, a lipid, a phospholipid, a fatty acid, a cholesterol, a poly-ethylene glycol, a nuclear localization signal, and/or a targeting molecule.

11. A nanoparticle comprising the peptide according to claim 1 and a cargo molecule.

12. The nanoparticle according to claim 11, wherein the cargo molecule is selected from the group consisting of a nucleic acid, a peptide, a protein, a lipid, a small molecule, a pharmaceutically active agent, and mixture of any thereof.

13. The nanoparticle according to claim 11, wherein the cargo molecule is a nucleic acid molecule selected from the group consisting of a DNA molecule, a RNA molecule, a PNA molecule, a siRNA molecule, a PMO molecule, an antisense molecule, a LNA molecule, a mcDNA molecule, a miRNA molecule, a CRISPR/Cas9 molecule, a plasmid, a ribozyme, an aptamer, a spiegelmer and a decoy molecule.

14. The nanoparticle according to claim 11, wherein the size of the nanoparticle is between 50 and 300 nm and/or wherein the cargo molecule is covalently or non-covalently bound to the peptide.

15. A pharmaceutical composition comprising the nanoparticle according to claim 11 and a pharmaceutically acceptable carrier.

16. A method for delivering cargo molecules into cells in vitro, comprising a step of putting said cells into contact with nanoparticles according to claim 11 said nanoparticles comprising said cargo molecules.

17. A method for delivering cargo molecules into tissues and/or organs ex vivo, comprising a step of putting said tissues and/or organs into contact with nanoparticles according to claim 11, said nanoparticles comprising said cargo molecules.

* * * * *

SEQUENCE LISTING

```
<160> NUMBER OF SEQ ID NOS: 22

<210> SEQ ID NO 1
<211> LENGTH: 16
<212> TYPE: PRT
<213> ORGANISM: artificial sequence
<220> FEATURE:
<223> OTHER INFORMATION: CPP1

<400> SEQUENCE: 1

Leu Leu Trp Arg Leu Trp Arg Leu Leu Trp Arg Leu Trp Arg Leu Leu
1               5                   10                  15

<210> SEQ ID NO 2
<211> LENGTH: 15
<212> TYPE: PRT
<213> ORGANISM: artificial sequence
<220> FEATURE:
<223> OTHER INFORMATION: CPP2

<400> SEQUENCE: 2

Leu Leu Arg Leu Leu Arg Trp Trp Trp Arg Leu Leu Arg Leu Leu
1               5                   10                  15

<210> SEQ ID NO 3
<211> LENGTH: 14
<212> TYPE: PRT
<213> ORGANISM: artificial sequence
<220> FEATURE:
<223> OTHER INFORMATION: CPP3

<400> SEQUENCE: 3

Leu Leu Arg Leu Leu Arg Trp Trp Arg Leu Leu Arg Leu Leu
```

<210> SEQ ID NO 4
<211> LENGTH: 16
<212> TYPE: PRT
<213> ORGANISM: artificial sequence
<220> FEATURE:
<223> OTHER INFORMATION: CPP4

<400> SEQUENCE: 4

Leu Leu Arg Leu Leu Arg Trp Trp Trp Trp Arg Leu Leu Arg Leu Leu
1               5                   10                  15

<210> SEQ ID NO 5
<211> LENGTH: 21
<212> TYPE: DNA
<213> ORGANISM: artificial sequence
<220> FEATURE:
<223> OTHER INFORMATION: siRNA

<400> SEQUENCE: 5
cuuacgcuga guacuucgat t                                             21

<210> SEQ ID NO 6
<211> LENGTH: 21
<212> TYPE: DNA
<213> ORGANISM: artificial sequence
<220> FEATURE:
<223> OTHER INFORMATION: siRNA

<400> SEQUENCE: 6
caucaucccu gccucuacut t                                             21

<210> SEQ ID NO 7
<211> LENGTH: 21
<212> TYPE: DNA
<213> ORGANISM: artificial sequence
<220> FEATURE:
<223> OTHER INFORMATION: siRNA

<400> SEQUENCE: 7
cagaucucgg ugaacgaugt t                                             21

<210> SEQ ID NO 8
<211> LENGTH: 23
<212> TYPE: DNA
<213> ORGANISM: artificial sequence
<220> FEATURE:
<223> OTHER INFORMATION: siRNA

<400> SEQUENCE: 8
aaccacucaa cuuuuuccca att                                           23

<210> SEQ ID NO 9
<211> LENGTH: 21
<212> TYPE: DNA
<213> ORGANISM: artificial sequence
<220> FEATURE:
<223> OTHER INFORMATION: primer

<400> SEQUENCE: 9
tccattccat cacggttttg g                                             21

<210> SEQ ID NO 10
<211> LENGTH: 21
<212> TYPE: DNA

```
<213> ORGANISM: artificial sequence
<220> FEATURE:
<223> OTHER INFORMATION: primer

<400> SEQUENCE: 10
gctatgtctc cagaatgtag c                                          21

<210> SEQ ID NO 11
<211> LENGTH: 21
<212> TYPE: DNA
<213> ORGANISM: artificial sequence
<220> FEATURE:
<223> OTHER INFORMATION: primer

<400> SEQUENCE: 11
gccaaggtca tccatgacaa c                                          21

<210> SEQ ID NO 12
<211> LENGTH: 21
<212> TYPE: DNA
<213> ORGANISM: artificial sequence
<220> FEATURE:
<223> OTHER INFORMATION: primer

<400> SEQUENCE: 12
gaggagtggg tgtcgctgtt g                                          21

<210> SEQ ID NO 13
<211> LENGTH: 14
<212> TYPE: PRT
<213> ORGANISM: artificial sequence
<220> FEATURE:
<223> OTHER INFORMATION: CPP1-1

<400> SEQUENCE: 13

Leu Trp Arg Leu Trp Arg Leu Leu Trp Arg Leu Trp Arg Leu
1               5                   10

<210> SEQ ID NO 14
<211> LENGTH: 11
<212> TYPE: PRT
<213> ORGANISM: artificial sequence
<220> FEATURE:
<223> OTHER INFORMATION: CPP2-1

<400> SEQUENCE: 14

Leu Arg Leu Arg Trp Trp Trp Arg Leu Arg Leu
1               5                   10

<210> SEQ ID NO 15
<211> LENGTH: 13
<212> TYPE: PRT
<213> ORGANISM: artificial sequence
<220> FEATURE:
<223> OTHER INFORMATION: CPP2-2

<400> SEQUENCE: 15

Leu Leu Arg Leu Arg Trp Trp Trp Arg Leu Arg Leu Leu
1               5                   10

<210> SEQ ID NO 16
<211> LENGTH: 13
<212> TYPE: PRT
<213> ORGANISM: artificial sequence
<220> FEATURE:
<223> OTHER INFORMATION: CPP2-3
```

```
<400> SEQUENCE: 16

Leu Arg Leu Leu Arg Trp Trp Trp Arg Leu Leu Arg Leu
1               5                   10

<210> SEQ ID NO 17
<211> LENGTH: 18
<212> TYPE: PRT
<213> ORGANISM: artificial sequence
<220> FEATURE:
<223> OTHER INFORMATION: C6M1

<400> SEQUENCE: 17

Arg Leu Trp Arg Leu Leu Trp Arg Leu Trp Arg Arg Leu Trp Arg Leu
1               5                   10                  15

Leu Arg

<210> SEQ ID NO 18
<211> LENGTH: 17
<212> TYPE: PRT
<213> ORGANISM: artificial sequence
<220> FEATURE:
<223> OTHER INFORMATION: C6M1-L

<400> SEQUENCE: 18

Arg Leu Trp Arg Leu Trp Arg Leu Trp Arg Arg Leu Trp Arg Leu Leu
1               5                   10                  15

Arg

<210> SEQ ID NO 19
<211> LENGTH: 13
<212> TYPE: PRT
<213> ORGANISM: artificial sequence
<220> FEATURE:
<223> OTHER INFORMATION: CPP1-4R

<400> SEQUENCE: 19

Arg Leu Leu Trp Arg Leu Trp Leu Trp Arg Leu Leu Arg
1               5                   10

<210> SEQ ID NO 20
<211> LENGTH: 18
<212> TYPE: PRT
<213> ORGANISM: artificial sequence
<220> FEATURE:
<223> OTHER INFORMATION: CPP1-6R

<400> SEQUENCE: 20

Arg Leu Leu Trp Arg Leu Trp Arg Leu Leu Trp Arg Leu Trp Arg Leu
1               5                   10                  15

Leu Arg

<210> SEQ ID NO 21
<211> LENGTH: 15
<212> TYPE: PRT
<213> ORGANISM: artificial sequence
<220> FEATURE:
<223> OTHER INFORMATION: CPP2-4R

<400> SEQUENCE: 21

Arg Leu Leu Arg Leu Leu Trp Trp Trp Leu Leu Arg Leu Leu Arg
1               5                   10                  15

<210> SEQ ID NO 22
<211> LENGTH: 17
```

```
<212> TYPE: PRT
<213> ORGANISM: artificial sequence
<220> FEATURE:
<223> OTHER INFORMATION: CPP2-6R

<400> SEQUENCE: 22

Arg Leu Leu Arg Leu Leu Arg Trp Trp Trp Arg Leu Leu Arg Leu Leu
1               5                   10                  15
Arg
```